United States Patent
Ganatra et al.

(10) Patent No.: US 11,098,295 B1
(45) Date of Patent: Aug. 24, 2021

(54) FCE MRNA CAPPING ENZYME COMPOSITIONS, METHODS AND KITS

(71) Applicant: New England Biolabs, Inc., Ipswich, MA (US)

(72) Inventors: Mehul Ganatra, Gloucester, MA (US); Siu-Hong Chan, Ipswich, MA (US); Christopher H. Taron, Essex, MA (US); G. B. Robb, Somerville, MA (US)

(73) Assignee: New England Biolabs, Inc., Ipswich, MA (US)

( * ) Notice: Subject to any disclaimer, the term of this patent is extended or adjusted under 35 U.S.C. 154(b) by 0 days.

(21) Appl. No.: 17/246,454

(22) Filed: Apr. 30, 2021

Related U.S. Application Data

(62) Division of application No. 17/160,256, filed on Jan. 27, 2021, now Pat. No. 11,028,379.

(51) Int. Cl.
| | |
|---|---|
| *C12N 9/16* | (2006.01) |
| *C12N 9/12* | (2006.01) |
| *C12N 7/00* | (2006.01) |
| *C12N 9/10* | (2006.01) |
| *A61K 39/245* | (2006.01) |
| *A61K 39/00* | (2006.01) |

(52) U.S. Cl.
CPC .............. *C12N 9/16* (2013.01); *A61K 39/245* (2013.01); *C12N 7/00* (2013.01); *C12N 9/1007* (2013.01); *C12N 9/1241* (2013.01); *C12Y 201/01056* (2013.01); *C12Y 207/0705* (2013.01); *C12Y 301/03033* (2013.01); *A61K 2039/53* (2013.01); *C07K 2319/21* (2013.01); *C12N 2710/16134* (2013.01)

(58) Field of Classification Search
None
See application file for complete search history.

(56) References Cited

U.S. PATENT DOCUMENTS

| 8,383,340 B2 | 2/2013 | Ketterer et al. |
| 9,428,535 B2 | 8/2016 | de Fougerolles et al. |
| 9,629,804 B2 | 4/2017 | Heartlein et al. |
| 2012/0251618 A1 | 10/2012 | Schrum et al. |
| 2016/0032316 A1 | 2/2016 | Weissman et al. |
| 2016/0038432 A1 | 2/2016 | DeRosa et al. |

FOREIGN PATENT DOCUMENTS

| WO | 2013151666 A2 | 10/2013 |
| WO | 2014152211 A1 | 9/2014 |

OTHER PUBLICATIONS

Beverly, et al., 2016, Analytical and Bioanalytical Chemistry 408:5021-5030.
Diamond, et al., Cytokine & Growth Factor Reviews, 2014 25: 543-550.
Kore, Nucleosides, Nucleotides, and Nucleic Acids, 2006, 25: 15 307-314.
Kore, Nucleosides, Nucleotides, and Nucleic Acids, 2006, 25: 15 337-340.
Looke, et al., 2011, BioTechniques, 50(5), 325-328.
Pichlmair, et al., Science 2006 314: 997-1001.
Ramanathan, Nucleic Acids Res. 2016 44: 7511-7526.
Sakhtah, et al. 2019. Appl Environ Microbiol 85:e00542-19. https://doi.org/10.1128/AEM.00542-19.
Shuman, 1989, J Biol Chem Jun. 5; 264(16):9690-5.
Wu, et al., 2004, BioTechniques, 36(1), 152-154.
Zheng, et al., RNA, 2008, 14: 2297-2304.
Kramer, et al, 2018, WIREs RNA 10(1)e1511.

*Primary Examiner* — Suzanne M Noakes
*Assistant Examiner* — Jae W Lee
(74) *Attorney, Agent, or Firm* — New England Biolabs, Inc

(57) ABSTRACT

The present disclosure relates to compositions, kits, and methods of making RNA vaccines having an appropriate cap structure. Systems, apparatus, compositions, and/or methods may include and/or use, in some embodiments, non-naturally occurring single-chain RNA capping enzymes. In some embodiments, an RNA capping enzyme may include an FCE variant having (a) an amino acid sequence at least 90% identical to positions 1 to 878 of SEQ ID NO: 1, and/or (b) one or more substitutions relative to SEQ ID NO: 1 at a position selected from positions corresponding to positions 215, 337, 572, 648, and 833 (e.g., a position selected from positions corresponding to position 215, 337, and 572) of SEQ ID NO: 1.

15 Claims, 11 Drawing Sheets

Specification includes a Sequence Listing.

FIG. 2

| 3' Promoter | α-MF | FCE | T$_{AOX1}$ | P$_{ilv5}$ + Zeo$^r$ | Ori_pUC | 5' Promoter | *Secreted protein expression (P. pastoris)* |

| 3' Promoter | malE | FCE | T$_{LAC4}$ | P$_{adh1}$ + amdS | Ori_pUC | 5' Promoter | *Cytoplasmic protein expression (K. lactis)* |

*Linear expression cassettes for targeted integration*

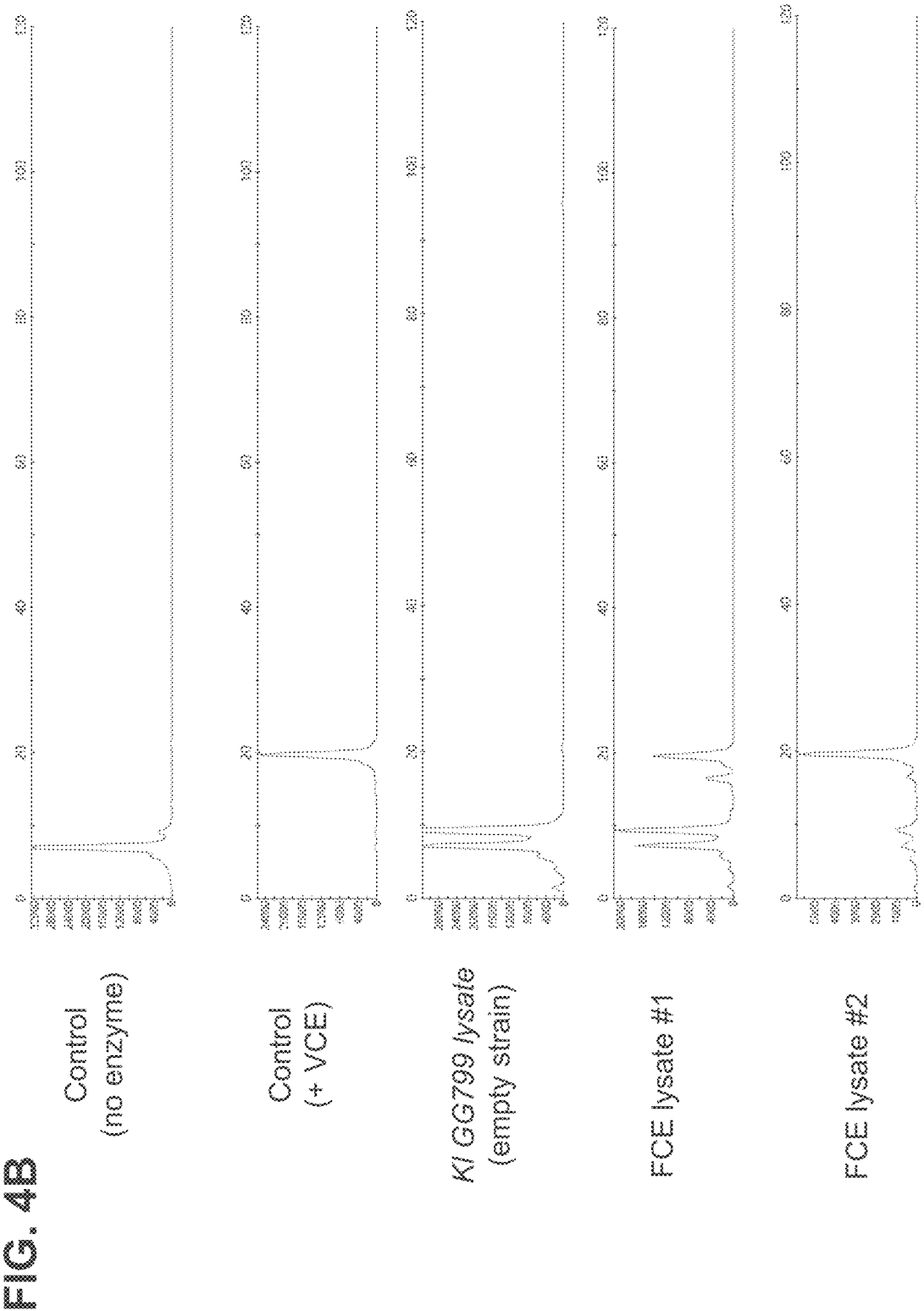

US 11,098,295 B1

FCE MRNA CAPPING ENZYME COMPOSITIONS, METHODS AND KITS

CROSS-REFERENCE TO RELATED APPLICATION

This application is a divisional of U.S. application Ser. No. 17/160,256 filed Jan. 27, 2021, the contents of which are hereby incorporated in their entirety by reference.

SEQUENCE LISTING STATEMENT

This disclosure includes a Sequence Listing submitted electronically in ascii format under the file name "NEB-438-US_ST25.txt". This Sequence Listing is incorporated herein in its entirety by this reference.

BACKGROUND

The potential for mRNA vaccines to transform the treatment of infectious diseases has gained considerable traction since it was first proposed. In addition, mRNA as a therapeutic modality may supplement functional therapeutic proteins that are not antigens, for example, erythropoietin, CFTR, or genome editing proteins (e.g., CRISPR-Cas9, meganucleases). Manufacturing mRNA may be cell-free and scalable. Once the sequence of a desired antigen is provided, the time required to produce clinical batches of vaccine might be weeks instead of months. Such rapid production may limit or even avert widespread outbreaks. In addition, mRNA alternatives to a number of protein replacement regimens are envisioned. Production of stable mRNA capable of efficient translation upon introduction to a subject may require an appropriate cap structure, such as a Cap 0 structure (m7Gppp5'N) at the 5' end. Capping by a capping enzyme may be desired or even required for production of an effective RNA vaccine. For example, a suitable cap structure may impact the stability and translatability of an RNA vaccine.

SUMMARY

Accordingly, needs have arisen for improved compositions, kits, and methods of making RNA vaccines having an appropriate cap structure. The present disclosure relates to systems, apparatus, compositions, and/or methods including non-naturally occurring single-chain RNA capping enzymes. In some embodiments, an RNA capping enzyme may include an FCE variant having (a) an amino acid sequence at least 90% identical to positions 1 to 878 of SEQ ID NO: 1, and/or (b) a substitution relative to SEQ ID NO: 1 at a position selected from positions corresponding to positions 215, 337, 572, 648, and 833 (e.g., a position selected from positions corresponding to position 215, 337, and 572) of SEQ ID NO: 1. An FCE variant, in some embodiments, may comprise a second substitution at a position (i) other than the position of the first substitution and (ii) corresponding to position 215, 337, 572, 648, or 833 of SEQ ID NO: 1. An FCE variant, in some embodiments, may comprise a third substitution at a position (iii) other than the position of the first and second substitutions and (iv) corresponding to position 215, 337, 572, 648, or 833 of SEQ ID NO: 1. An FCE variant, in some embodiments, may comprise a fourth substitution at a position (v) other than the position of the first, second and third substitutions and (vi) corresponding to position 215, 337, 572, 648, or 833 of SEQ ID NO: 1. In some embodiments, an FCE variant may have an amino acid sequence that is at least 90% identical, but not 100% identical to SEQ ID NO: 1. In some embodiments, an FCE variant may have an amino acid sequence that is at least 90% identical, but not 100% identical to SEQ ID NO: 1. An FCE variant (a) may have an amino acid sequence (a) at least 90% identical to SEQ ID NO: 26, and/or (b) may have an amino acid other than asparagine at a position selected from positions corresponding to positions X215, X337, X572, X648, and X833 of SEQ ID NO: 26.

In some embodiments, an FCE variant may include additional peptides (e.g., for sorting, processing, and/or purification of the catalytically active portion of the molecule). For example, an FCE variant may comprise a purification tag and/or a sorting signal. In some embodiments, an FCE variant may comprise, in an N-terminal to C-terminal direction, (a) a purification tag or sorting signal peptide, and (b)(i) an amino acid sequence at least 90% identical to positions 1 to 878 of SEQ ID NO: 1, and/or (ii) a substitution relative to SEQ ID NO: 1 at a position selected from positions corresponding to positions 215, 337, 572, 648, and 833. In some embodiments, an FCE variant may further comprise an insertion (e.g., a sorting signal or a purification tag) on the N-terminal side of the position corresponding to position 1 of SEQ ID NO: 1. In some embodiments, an FCE variant may further comprise an insertion (e.g., a sorting signal or a purification tag) on the C-terminal side of the position corresponding to position 878 of SEQ ID NO: 1.

Compositions, according to some embodiments, may include an FCE variant (e.g., any of the foregoing FCE variants) and a polynucleotide, wherein the polynucleotide comprises ribonucleotides and deoxyribonucleotides. A composition, according to some embodiments, may comprise an FCE variant (e.g., any of the foregoing FCE variants) and a polyribonucleotide. A composition may optionally comprise, for example, a cap, an NTP, a modified NTP, a buffer, S-adenosylmethionine, and/or an RNase inhibitor, according to some embodiments.

The present disclosure relates, in some embodiments, to FCE variant transcripts. For example, an FCE variant transcript may comprise a transcript (e.g., polynucleotide transcript comprising RNA) encoding an amino acid sequence having (a) at least 90% identical to positions 1 to 878 of SEQ ID NO: 1, and (b) a substitution relative to SEQ ID NO: 1 at a position selected from positions corresponding to positions 215, 337, 572, 648, and 833 (e.g., a position selected from positions corresponding to position 215, 337, and 572) of SEQ ID NO: 1, and (c) optionally, a cap. An amino acid sequence encoded by an FCE variant transcript, in some embodiments, may comprise a second substitution at a position (i) other than the position of the first substitution and (ii) corresponding to position 215, 337, 572, 648, or 833 of SEQ ID NO: 1. An amino acid sequence encoded by an FCE variant transcript, in some embodiments, may comprise a third substitution at a position (iii) other than the position of the first and second substitutions and (iv) corresponding to position 215, 337, 572, 648, or 833 of SEQ ID NO: 1. An amino acid sequence encoded by an FCE variant transcript, in some embodiments, may comprise a fourth substitution at a position (v) other than the position of the first, second and third substitutions and (vi) corresponding to position 215, 337, 572, 648, or 833 of SEQ ID NO: 1.

An FCE variant transcript, according to some embodiments, may comprise in a 5' to 3' direction, (I) a nucleotide sequence encoding a purification tag or a sorting signal peptide, and (II) an FCE variant transcript comprising, for example, a transcript encoding an amino acid sequence having (A) at least 90% identical to positions 1 to 878 of SEQ ID NO: 1, and (B) a substitution relative to SEQ ID NO: 1 at a position selected from positions corresponding to positions 215, 337, 572, 648, and 833 of SEQ ID NO: 1, and (C) optionally, a cap, wherein the purification tag or sorting signal peptide is operably linked to the FCE variant encoded by (II). In some embodiments, an FCE variant transcript may comprise in a 5' to 3' direction, (I) an FCE variant transcript comprising, for example, a transcript encoding an amino acid sequence having (A) at least 90% identical to positions 1 to 878 of SEQ ID NO: 1, and (B) a substitution relative to SEQ ID NO: 1 at a position selected from positions corresponding to positions 215, 337, 572, 648, and 833 of SEQ ID NO: 1, and (C) optionally, a cap, and (II) a nucleotide sequence encoding a purification tag or a sorting signal peptide, wherein the purification tag or sorting signal peptide is operably linked to the FCE variant encoded by (I). In some embodiments, an FCE variant transcript may encode an amino acid sequence further comprising an insertion (e.g., a sorting signal or a purification tag) on the N-terminal side of the position corresponding to position 1 of SEQ ID NO: 1 and/or on the C-terminal side of the position corresponding to position 878 of SEQ ID NO: 1. In some embodiments, an FCE variant transcript comprises (C) a cap (e.g., a natural cap, a dinucleotide cap, or a modified cap).

The present disclosure further relates to cells and cell-based and cell-free methods of producing FCE variants and FCE variant transcripts. For example, a cell may comprise one or more FCE variants and or one or more FCE variant transcripts. In some embodiments, a cell may comprise an FCE variant transcript may comprise a polynucleotide (e.g., polynucleotide transcript comprising RNA) encoding an amino acid sequence having (a) at least 90% identical to positions 1 to 878 of SEQ ID NO: 1, and (b) a substitution relative to SEQ ID NO: 1 at a position selected from positions corresponding to positions 215, 337, 572, 648, and 833 (e.g., a position selected from positions corresponding to position 215, 337, and 572) of SEQ ID NO: 1, and (c) optionally, a cap. A cell may comprise a genomic or an extra-genomic polynucleotide (e.g., a DNA expression vector or cassette) having a sequence encoding an FCE variant having (a) an amino acid sequence at least 90% identical to positions 1 to 878 of SEQ ID NO: 1, and/or (b) a substitution relative to SEQ ID NO: 1 at a position selected from positions corresponding to positions 215, 337, 572, 648, and 833 (e.g., a position selected from positions corresponding to position 215, 337, and 572) of SEQ ID NO: 1. A cell, in some embodiments, may be a eukaryotic cell, for example, a yeast cell.

The present disclosure further relates to methods of capping a target RNA. A capping method may comprise, for example, contacting (a) an FCE variant having (i) an amino acid sequence at least 90% identical to positions 1 to 878 of SEQ ID NO: 1, and (ii) a substitution at a position selected from positions corresponding to positions 215, 337, 572, 648, and 833 of SEQ ID NO: 1, (b) a target RNA (e.g., an uncapped RNA), and (c) one or more of a cap, an NTP, and a modified NTP, and optionally (d) a buffer, S-adenosylmethionine, and/or an RNase inhibitor, to form a capped target RNA. In some embodiments, contacting may comprise contacting at a temperature in the range of 37° C.-60° C. and/or for a time in the range of seconds to hours (e.g., 60 seconds to 16 hours). A target RNA may or may not be capped (e.g., before contacting). According to some embodiments, a method may comprise contacting a target RNA (e.g., a capped target RNA) with a decapping enzyme to form an uncapped target RNA, for example, prior to contacting the target RNA with the FCE variant. A method may further comprise contacting the capped target RNA with one or more pharmaceutically acceptable additives.

A method of producing an FCE variant may comprise, for example, contacting (a) an FCE variant transcript comprising an RNA encoding an amino acid sequence having (i) an amino acid sequence at least 90% identical to positions 1 to 878 of SEQ ID NO: 1, and (ii) a substitution at a position selected from positions corresponding to positions 215, 337, 572, 648, and 833 of SEQ ID NO: 1 with (b) an expression system (e.g., a cell-based or cell-free expression system).

BRIEF DESCRIPTION OF THE FIGURES

FIG. 1A shows a general map of pD912 (ATUM, formerly DNA 2.0) and FIG. 1B shows a general map of pKLMF-EK (New England Biolabs) used to assemble plasmids containing FCE, α-mating factor and MBP-fusion constructs respectively.

FIG. 2 shows schematically the linear integrative expression cassettes that were prepared by SacI-HF restriction digestion or PCR from the assembled plasmids as a DNA template. The assembled plasmids and linear cassettes have the following design: GAP or LAC4 promoter, followed by the α-mating factor pre-pro domain (secretion) or malE gene (cytoplasmic), FCE with carboxy-terminal His-tag; AOX1 terminator sequence ($T_{AOX1}$) or K. lactis LAC4 transcription terminator (TT); zeocin resistance gene under control of the ILV5 promoter ($P_{ILV5}$+Zeo$^r$) or a fungal acetamidase selectable marker gene (amdS) expressed from the yeast ADH1 promoter ($P_{ADH1}$); the sequence of an E. coli origin of replication (Ori_pUC); flanking sequences for the targeted integration (3' Promoter fragment contains the sequence of the actual promoter). pKLMF-EK also contains an ampicillin resistance gene ($Ap^R$) for selection in E. coli.

FIG. 3A shows secreted expression of FCE wild type (WT) and individual FCE N-glycan variants in P. pastoris cells transformed with constructs containing GAP promoter. Transformants were grown in Buffered Minimal Glycerol medium, BMGY with 1% glycerol at 30° C. for 48 hours. The spent culture medium was harvested, concentrated and buffer exchanged. After overnight digestion with Endo Hf, the spent media was analyzed by SDS-PAGE on a 4-20% polyacrylamide gel followed by western blotting with a His-tag antibody. Lanes 1, 2: FCE-WT −/+Endo Hf, respectively; Lanes 3, 4: FCE-N215Q −/+Endo Hf, respectively; Lanes 5, 6: FCE-N337Q −/+Endo Hf, respectively; Lanes 7, 8: FCE-N572Q −/+Endo Hf, respectively; Lanes 9, 10: P. pastoris (empty strain) −/+Endo Hf, respectively. FIG. 3B shows cytoplasmic expression of MBP-FCE in K. lactis cells transformed with a construct containing the K. lactis LAC4 promoter. The transformants were grown in yeast extract peptone (YEP) medium with 2% galactose at 30° C. for 48 hours. Cells were harvested, and cell lysates were prepared by sonication and analyzed by SDS-PAGE on a 4-20% polyacrylamide gel, followed by western blotting with a His-tag antibody. Lanes 1, 2—cell lysates of K. lactis transformants #1 and #2 expressing MBP-FCE; lane 3—control K. lactis cell lysate.

FIGS. 4A and 4B show the activity of expressed FCE proteins. FIG. 4A shows spent culture media from P. pastoris cells treated with Endo Hf. FIG. 4B shows cell lysates from *K. lactis* cells. The activity was assayed using an in vitro mRNA capping assay as described in Examples section V.

FIG. 7A is a Simply Blue Safe Stained gel.

FIG. 7B is a corresponding Western blot.

BRIEF DESCRIPTION OF THE SEQUENCES

Figure 1A:
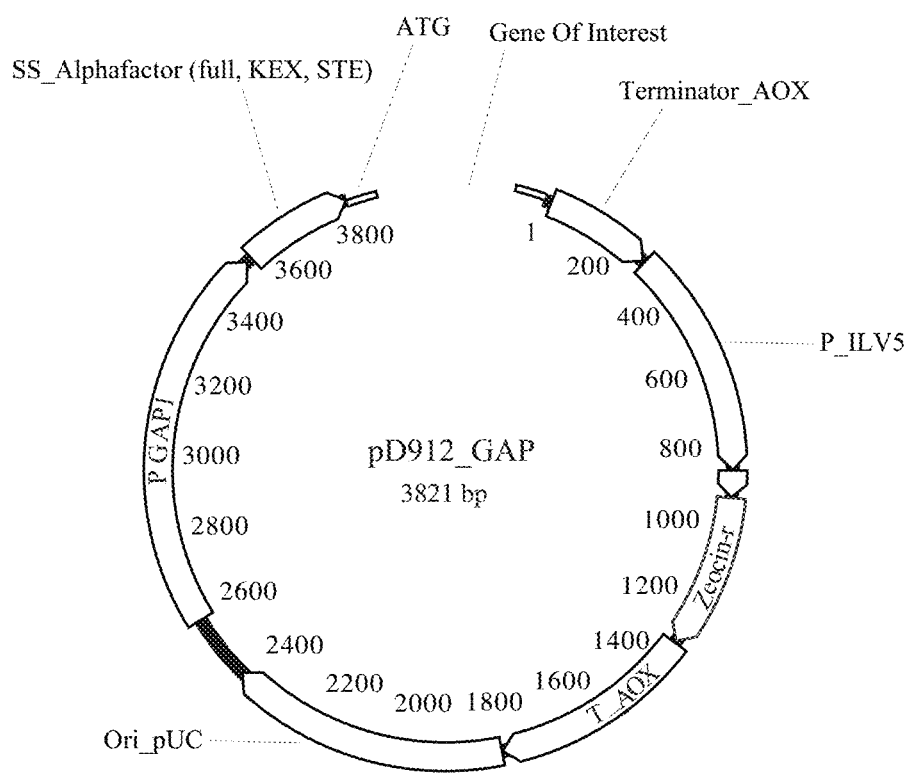
FIGS. 1A and 1B show general maps of yeast expression vectors.

Sequences of example polynucleotides and polypeptides, according to some embodiments, are elaborated in the SEQUENCE LISTING, in which:

SEQ ID NO: 1 illustrates an amino acid sequence of an FCE variant having a C-terminal 8×His tag (879-886) in which positions 215, 337, 572, 648, and/or 833 may be glycosylated or replaced with any other amino acid (e.g., glutamine);

SEQ ID NO: 2 illustrates an amino acid sequence of an FCE variant having a region with a maltose binding protein (MBP), Linker, and enterokinase (EK) cleavage sequence (DDDK) (1-388) and a C-terminal 8×His tag (1267-1274);

SEQ ID NO: 3 illustrates a forward primer for amplification of an FCE variant in which positions 1-20 overlap with the signal peptide sequence in the pD912 vector (SEQ ID NO: 24 or 26);

SEQ ID NO: 4 illustrates a reverse primer for amplification of an FCE variant in which positions 1-20 overlap with the $T_{AOX1}$ sequence in the pD912 vector (SEQ ID NO: 24 or 26);

SEQ ID NO: 5 illustrates a forward primer for amplification of a pD912 vector fragment;

SEQ ID NO: 6 illustrates a reverse primer for amplification of a pD912 vector fragment;

SEQ ID NO: 7 illustrates a forward primer adapted (e.g., at positions 11-13) for modifying the codon corresponding to position 215 of SEQ ID NO: 1 from asparagine to glutamine;

SEQ ID NO: 8 illustrates a reverse primer adapted for modifying the codon corresponding to position 215 of SEQ ID NO: 1 from asparagine to glutamine;

SEQ ID NO: 9 illustrates a forward primer adapted (e.g., at positions 11-13) for modifying the codon corresponding to position 337 of SEQ ID NO: 1 from asparagine to glutamine;

SEQ ID NO: 10 illustrates a reverse primer adapted for modifying the codon corresponding to position 337 of SEQ ID NO: 1 from asparagine to glutamine;

SEQ ID NO: 11 illustrates a forward primer adapted (e.g., at positions 11-13) for modifying the codon corresponding to position 572 of SEQ ID NO: 1 from asparagine to glutamine;

SEQ ID NO: 12 illustrates a reverse primer adapted for modifying the codon corresponding to position 572 of SEQ ID NO: 1 from asparagine to glutamine;

SEQ ID NO: 13 illustrates a forward primer adapted (e.g., at positions 11-13) for modifying the codon corresponding to position 648 of SEQ ID NO: 1 from asparagine to glutamine;

SEQ ID NO: 14 illustrates a reverse primer adapted for modifying the codon corresponding to position 648 of SEQ ID NO: 1 from asparagine to glutamine;

SEQ ID NO: 15 illustrates a forward primer adapted (e.g., at positions 11-13) for modifying the codon corresponding to position 833 of SEQ ID NO: 1 from asparagine to glutamine;

SEQ ID NO: 16 illustrates a reverse primer adapted for modifying the codon corresponding to position 833 of SEQ ID NO: 1 from asparagine to glutamine;

SEQ ID NO: 17 illustrates a forward primer for amplification of an FCE variant in which positions 1-20 overlap with the malE sequence in the pKLMF-EK vector;

SEQ ID NO: 18 illustrates a reverse primer for amplification of an FCE variant in which positions 1-20 overlap with multiple cloning site sequence in the pKLMF-EK vector;

SEQ ID NO: 19 illustrates a forward primer for amplification of a pKLMF-EK vector fragment;

SEQ ID NO: 20 illustrates a reverse primer for amplification of a pKLMF-EK vector fragment;

SEQ ID NO: 21 illustrates a forward primer for amplification of an assembled linear expression cassette of pKLMF-EK-FCE;

SEQ ID NO: 22 illustrates a reverse primer for amplification of an assembled linear expression cassette of pKLMF-EK-FCE;

SEQ ID NO: 23 illustrates a substrate RNA for in vitro capping reactions;

SEQ ID NO: 24 illustrates a nucleotide sequence of an expression plasmid, namely pD912-FCE(N215Q/N337Q/N572Q) expression plasmid;

SEQ ID NO: 25 illustrates a fully processed mature FCE variant protein with asparagine to glutamine substitutions at positions corresponding to positions 215, 337, and 572 of SEQ ID NO: 1;

SEQ ID NO: 26 illustrates a nucleotide sequence of an expression plasmid, namely pD912-FCE (N215Q/N337Q/N572Q N648Q/N833Q) expression plasmid;

SEQ ID NO: 27 illustrates a fully processed mature FCE variant protein with asparagine to glutamine substitutions at positions corresponding to positions 215, 337, 572, 648, AND 833 of SEQ ID NO: 1; and SEQ ID NO: 28 illustrates an amino acid sequence of an FCE variant in which positions 215, 337, 572, 648 and/or 833 may comprise any amino acid (e.g., optionally, any amino acid other than asparagine.

DETAILED DESCRIPTION

Aspects of the present disclosure can be further understood in light of the embodiments, section headings, figures, descriptions and examples, none of which should be construed as limiting the entire scope of the present disclosure in any way. Accordingly, the claims set forth below should be construed in view of the full breadth and spirit of the disclosure.

Each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

Unless otherwise defined, all technical and scientific terms used herein have the same meaning as commonly understood by one of ordinary skill in the art to which this disclosure belongs. Still, certain terms are defined herein with respect to embodiments of the disclosure and for the sake of clarity and ease of reference.

Sources of commonly understood terms and symbols may include: standard treatises and texts such as Kornberg and Baker, DNA Replication, Second Edition (W.H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Eckstein, editor, Oligonucleotides and Analogs: A Practical Approach (Oxford University Press, New York, 1991); Gait, editor, Oligonucleotide Synthesis: A Practical Approach (IRL Press, Oxford, 1984); Singleton, et al., Dictionary of Microbiology and Molecular biology, 2d ed., John Wiley and Sons, New York (1994), and Hale & Markham, the Harper Collins Dictionary of Biology, Harper Perennial, N.Y. (1991) and the like.

In the context of the present disclosure, the singular forms "a" and "an" include plural referents unless the context clearly dictates otherwise. For example, the term "a protein" refers to one or more proteins, i.e., a single protein and multiple proteins. It is further noted that the claims can be drafted to exclude any optional element. As such, this statement is intended to serve as antecedent basis for use of such exclusive terminology as "solely," "only" and the like in connection with the recitation of claim elements or use of a "negative" limitation.

Numeric ranges are inclusive of the numbers defining the range. All numbers should be understood to encompass the midpoint of the integer above and below the integer i.e., the number 2 encompasses 1.5-2.5. The number 2.5 encompasses 2.45-2.55 etc. When sample numerical values are provided, each alone may represent an intermediate value in a range of values and together may represent the extremes of a range unless specified.

In the context of the present disclosure, "active" with reference to an enzyme refers to detectable catalytic activity by any available assay including those set forth in the Examples. For example, an active FCE capping enzyme has at least detectable RNA-triphosphatase activity, at least detectable RNA guanylyltransferase activity, or at least detectable RNA N7-guanine methyltransferase activity.

Each catalytic activity may be tested separately and/or in combination. Techniques for detecting TPase activity include, for example, combining the subject enzyme with $\gamma$-$^{32}$P-poly(A) RNA, separating reaction products using thin layer chromatography, excising Pi spots and subjecting to scintillation counting to measure Pi (and indirectly pp-poly(A) RNA) release from ppp-poly(A) RNA. Techniques for detecting GTase activity include an enzyme-GMP intermediate assay in which, for example, the subject enzyme is combined with $\alpha$-$^{32}$P-GTP, reaction products are separated by SDS-PAGE, and the enzyme-GMP covalent intermediate formed (if any) is detected (e.g., by autoradiography). This activity can also be assessed in a cap formation reaction in which, for example, the subject enzyme is combined with $\alpha$-$^{32}$P-GTP and poly(A) RNA and the reaction products are analyzed by TCA precipitation, filter binding, and scintillation counting (measuring the amount of Gppp-poly(A) RNA). Techniques for detecting MTase activity include combining a radiolabeled capped poly(A) RNA (e.g., $\alpha$-$^{32}$P-GTP with poly(A) RNA) and VCE to produce G*ppp-poly(A) RNA, contacting that product with SAM and the subject enzyme, digesting with P1 nuclease, separating reaction products by thin layer chromatography, and analyzing excised spots by scintillation counting to measure the amount of m7GpppA from poly(A) RNA (JBC (1989) 264:9690-9695). MTase activity may also be detected by combining the subject enzyme with GpppA (New England Biolabs, Inc.) and $^3$H-S-adenosyl methionine, separating reaction products by thin layer chromatography, and analyzing excised bands by scintillation counting to measure amount of m7GpppA formed (RNA (2008) 14: 2297-2304).

In the context of the present disclosure, "buffer" and "buffering agent" refer to a chemical entity or composition that itself resists and, when present in a solution, allows such solution to resist changes in pH when such solution is contacted with a chemical entity or composition having a higher or lower pH (e.g., an acid or alkali). Examples of suitable non-naturally occurring buffering agents that may be used in disclosed compositions, kits, and methods include, for example, Tris, HEPES, TAPS, MOPS, tricine, or MES.

In the context of the present disclosure, "cap" refers to a natural cap, such as $^7$mG, and to a compound of the general formula R3p$_3$N1-[p-N](x), where R3 is a guanine, adenine, cytosine, uridine or analogs thereof (e.g., N$^7$-methylguanosine; m$^7$G), p$_3$ is a triphosphate linkage, N1 and Nx are ribonucleosides, x is 0-8 and p is, independently for each position, a phosphate group, a phosphorothioate, a phosphorodithioate, an alkylphosphonate, an arylphosphonate, or a N-phosphoramidate linkage. R3 may have an added label at the 2' or 3' position of the ribose, and, in some embodiments, the label may be an oligonucleotide, a detectable label such as a fluorophore, or a capture moiety such as biotin or desthiobiotin, where the label may be optionally linked to the ribose of the nucleotide by a linker, for example. See, e.g., WO 2015/085142. A cap may have a cap 0 structure, a cap 1 structure or a cap 2 structure (e.g., as reviewed in Ramanathan, Nucleic Acids Res. 2016 44: 7511-7526), depending on which enzymes and/or whether SAM is present in the capping reaction.

Caps include dinucleotide cap analogs, e.g., of formula m$^7$G(5')p3(5')G, in which a guanine nucleotide (G) is linked via its 5'OH to the triphosphate bridge. In some dinucleotide caps the 3'-OH group is replaced with hydrogen or OCH$_3$ (U.S. Pat. No. 7,074,596; Kore, Nucleosides, Nucleotides, and Nucleic Acids, 2006, 25: 15 307-14; and Kore, Nucleosides, Nucleotides, and Nucleic Acids, 2006, 25: 337-40). Dinucleotide caps include m$^7$G(5')p$_3$G, 3'-OMe-m$^7$G(5') p$_3$G (ARCA). Caps also include trinucleotide cap analogs (defined below) as well as other, longer, molecules (e.g., cap that have four, five or six or more nucleotides joined to the triphosphate bridge). In a cap analog, the 2' and 3' groups on the ribose of the m$^7$G may be independently selected O-alkyl (e.g., O-methyl), halogen, a linker, hydrogen or a hydroxyl and the sugars 20 in N1 and NX may be independently selected from ribose, deoxyribose, 2'-O-alkyl, 2'-O-methoxyethyl, 2'-O-allyl, 2'-O-alkylamine, 2'-fluororibose, and 2'-deoxyribose. Ni and NX may independently (for each position) comprise a base selected from adenine, uridine, guanine, or cytidine or analogs of adenine, uridine, guanine, or cytidine, and nucleotide modifications can be selected from N$^6$-methyladenine, N$^1$-methyladenine,N$^6$-2'-Odimethyladenosine, pseudouridine, N1-methylpseudouridine, 5-iodouridine, 4-thiouridine, 2-thiouridine, 5-methyluridine, pseudoisocytosine, 5-methoxycytosine, 2-thiocytosine, 5-hydroxycytosine, N$^4$-methylcytosine, 5-hydroxymethylcytosine, hypoxanthine, N1-methylguanine, O$^6$-methylguanine, 1-methyl-guanosine, N$^2$-methylguanosine, N$^2$,N$^2$-dimethyl-guanosine, 2-methyl-2'-O-methyl-guanosine, N$^2$,N$^2$-dimethyl-2'-O-methyl-guanosine, 1-methyl-2'-O-methyl-guanosine, N$^2$,N$^7$-dimethyl-2'-O-methyl-guanosine, and isoguanineadenine.

In the context of the present disclosure, "capping" refers to the addition of a cap onto the 5' end of an RNA. Caps may be added at the 5' end of an RNA (e.g., an uncapped RNA transcript) chemically or enzymatically apart from transcription or co-transcriptionally to yield a 5' capped RNA. Capping may or may not be reversible.

In the context of the present disclosure, "decapping enzyme" refers to an enzyme that removes a cap from an RNA, leaving the RNA with a 5' monophosphate, but otherwise unchanged. Decapping enzymes may have pyrophosphohydrolase activity. Examples of decapping enzymes include enzymes in the Nudix hydrolase family (e.g., RppH, DCP1/DCP2 complex, NUDT16, African swine fever virus decapping enzyme), DXO family (e.g., Dxolp, Railp), histidine triad family (e.g., DCPS, Fhit), and Apa-H-like phosphatase. Examples of decapping enzymes are described in Kramer and McLennan, 2019, WIREs RNA 10(1)e1511.

In the context of the present disclosure, "expression system" refers to systems for producing a protein from a polynucleotide template comprising components to produce the protein according to an RNA template (e.g., enzymes, amino acids, an energy source), (optionally) components to produce the RNA template according to another RNA template or a DNA template (e.g., enzymes, nucleotides, an energy source). An expression system may comprise a bacterial (e.g., *Escherichia coli*) or yeast (e.g., *Kluyveromyces lactis* or *Pichia pastoris*) expression system in which the protein is encoded by an RNA or DNA template within an expression cassette, a plasmid or other expression vector. An expression system may comprise a viral expression system in which the protein is encoded by an RNA or DNA template (e.g., in an expression cassette) within a viral genome or viral expression vector. Examples of cell-free expression systems may include or comprise cell extracts of *Escherichia coli* S30, rabbit reticulocytes or wheat germ, PURE-EXPRESS® (New England Biolabs, Ipswich, Mass.), an insect cell extract system (e.g., Promega #L1101), or HeLa cell lysate-based protein expression systems (e.g., Thermo Fisher Scientific #88882). An expression cassette may comprise, in some embodiments, an expression control sequence (e.g., promoter), a coding sequence encoding the gene product (e.g., protein) of interest (e.g., a vaccinia capping enzyme fusion), and/or one or more termination sequences (e.g., terminators). An expression control sequence (e.g., promoter) may comprise any promoter operative in a desired expression system, including, for example, a GAP promoter, an AOX1 promoter, a LAC4 promoter, a P350 hybrid promoter, a T7 promoter, a T5 promoter, a Ptac promoter, a Ptrc promoter, ParaBAD promoter, a PrhaBAD promoter, a Tet promoter or a PhoA phosphate-starvation promoter.

In the context of the present disclosure, "FCE" refers to a single-chain enzyme having RNA capping activity and having the amino acid sequence of positions 1 to 878 of SEQ ID NO:1.

In the context of the present disclosure, "FCE variant" (or "variant FCE") refers to a non-naturally occurring, single-chain enzyme having (a) RNA capping activity and (b) less than 100% amino acid sequence identity to a naturally occurring single-chain RNA capping enzyme and/or a non-naturally occurring chemical modification (e.g., a polypeptide fused to its amino terminal or carboxy terminal end or other chemical modification). A variant amino acid sequence may have at least 80%, at least 85%, at least 90%, at least 95%, at least 97%, at least 98% or at least 99% identity to the amino acid sequence of FCE. Sequence differences may include insertions or deletions extending and/or shortening the N- and/or C-terminal ends. An FCE variant may have an amino acid sequence having less than 100% identity to positions 1 to 878 of SEQ ID NO: 1. An FCE variant may have, for example, an amino acid sequence having one or more substitutions with respect to positions 1 to 878 of SEQ ID NO: 1 and having at least 90%, at least 92%, at least 94%, at least 96%, or at least 98% identity with positions 1 to 878 of SEQ ID NO: 1. An FCE variant may have, for example, an amino acid sequence having one or more substitutions with respect to SEQ ID NO: 1 and having at least 90%, at least 92%, at least 94%, at least 96%, or at least 98% identity with SEQ ID NO: 1 or SEQ ID NO: 2.

An FCE variant may have an amino acid sequence having less than 100% identity to positions 1 to 878 of SEQ ID NO: 1. An FCE variant may have, for example, an amino acid sequence having one or more substitutions with respect to positions 389 to 1266 of SEQ ID NO: 2 and having at least 90%, at least 92%, at least 94%, at least 96%, or at least 98% identity with positions 389 to 1266 of SEQ ID NO: 2. FCE variants may comprise one or more substitutions that impact glycosylation of the protein. For example, an FCE variant may comprise one or more substitutions at one or more positions selected from positions corresponding to N215, N337, N572, N648, and N833 of SEQ ID NO: 1 or selected from positions corresponding to N603, N725, N960, N1036, and N1221 of SEQ ID NO: 2. Substitutions at positions corresponding to N215, N337, N572, N648, and N833 of SEQ ID NO: 1 and positions corresponding to N603, N725, N960, N1036, and N1221 of SEQ ID NO: 2 may be a deletion or any amino acid other than asparagine, but may be selected to retain one or more properties of the asparagine replaced. For example, replacement amino acids for asparagine may be glutamine. In some embodiments, an FCE variant may comprise an amino acid sequence having (a) at least 90% identity to positions 1-214 of SEQ ID NO:1, (b) at least 90% identity to positions 216-336 of SEQ ID NO:1, (c) at least 90% identity to positions 338-571 of SEQ ID NO:1, (d) at least 90% identity to positions 573-647 of SEQ ID NO:1, (e) at least 90% identity to positions 649-832 of SEQ ID NO:1, (f) at least 90% identity to positions 834-878 of SEQ ID NO:1, and (g) a substitution at a position corresponding to position 215, 337, 572, 648, or 833 of SEQ ID NO: 1 (e.g., a deletion or any amino acid other than asparagine). In some embodiments, an FCE variant may comprise an amino acid sequence having (a) at least 90% identity to positions 389-602 of SEQ ID NO:2, (b) at least 90% identity to positions 604-724 of SEQ ID NO:2, (c) at least 90% identity to positions 726-959 of SEQ ID NO:2, (d) at least 90% identity to positions 961-1035 of SEQ ID NO:2, (e) at least 90% identity to positions 1037-1220 of SEQ ID NO:2, (f) at least 90% identity to positions 1222-1266 of SEQ ID NO:2, and (g) a substitution at a position corresponding to position 603, 725, 960, 1036, or 1221 of SEQ ID NO: 2 (e.g., a deletion or any amino acid other than asparagine). In some embodiments, an FCE variant may comprise a polypeptide having the amino acid sequence of SEQ ID NO:25 or SEQ ID NO:27.

In the context of the present disclosure, "in vitro transcription" (IVT) refers to a cell-free reaction in which a DNA template is copied by a DNA-directed RNA polymerase (typically a bacteriophage polymerase) to produce a product that comprises one or more RNA molecules that have been copied from the template.

In the context of the present disclosure, "modified nucleotide" refers to nucleotides having a modification on the sugars (e.g., 2'-fluororibose, ribose, 2'-deoxyribose, arabinose, and hexose); and/or in the phosphate groups (e.g., phosphorothioates and 5'-N-phosphoramidite linkages); and/or in the nucleotide base (e.g., as described in U.S. Pat. No. 8,383,340; WO 2013/151666; U.S. Pat. No. 9,428,535 B2; US 2016/0032316).

In the context of the present disclosure, "non-naturally occurring" refers to a polynucleotide, polypeptide, carbohydrate, lipid, or composition that does not exist in nature.

Such a polynucleotide, polypeptide, carbohydrate, lipid, or composition may differ from naturally occurring polynucleotides polypeptides, carbohydrates, lipids, or compositions in one or more respects. For example, a polymer (e.g., a polynucleotide, polypeptide, or carbohydrate) may differ in the kind and arrangement of the component building blocks (e.g., nucleotide sequence, amino acid sequence, or sugar molecules). A polymer may differ from a naturally occurring polymer with respect to the molecule(s) to which it is linked. For example, a "non-naturally occurring" protein may differ from naturally occurring proteins in its secondary, tertiary, or quaternary structure, by having a chemical bond (e.g., a covalent bond including a peptide bond, a phosphate bond, a disulfide bond, an ester bond, and ether bond, and others) to a polypeptide (e.g., a fusion protein), a lipid, a carbohydrate, or any other molecule. Similarly, a "non-naturally occurring" polynucleotide or nucleic acid may contain one or more other modifications (e.g., an added label or other moiety) to the 5'-end, the 3' end, and/or between the 5'- and 3'-ends (e.g., methylation) of the nucleic acid. A "non-naturally occurring" composition may differ from naturally occurring compositions in one or more of the following respects: (a) having components that are not combined in nature, (b) having components in concentrations not found in nature, (c) omitting one or components otherwise found in naturally occurring compositions, (d) having a form not found in nature, e.g., dried, freeze dried, crystalline, aqueous, and (e) having one or more additional components beyond those found in nature (e.g., buffering agents, a detergent, a dye, a solvent or a preservative).

In the context of the present disclosure, "polymerase" refers to an enzyme that synthesizes a polynucleotide from NTPs with or without a template. Examples of enzymes include T3 RNA polymerase, T7 RNA polymerase, SP6 polymerase, among others and variants thereof including thermostable variants (e.g., International Application No. PCT/US2017/013179 and U.S. application Ser. No. 15/594,090).

In the context of the present disclosure, a "single-chain RNA capping enzyme" refers to a capping enzyme in which a single polypeptide chain as a monomer displays RNA triphosphatase (TPase), guanylyltransferase (GTase) and guanine-N7 methyltransferase (N7 MTase) activities. Faustovirus, mimivirus and moumouvirus capping enzymes are examples of single-chain RNA capping enzymes. For clarity, VCE is a heterodimer and, as such, is not a single-chain RNA capping enzyme.

In the context of the present disclosure, a "substitution" at a position in a comparator amino acid sequence refers to any difference at that position relative to the corresponding position in a reference sequence, including a deletion, an insertion, and a different amino acid, where the comparator and reference sequences are at least 80% identical to each other. A substitution in a comparator sequence, in addition to being different than the reference sequence, may differ from all corresponding positions in naturally occurring sequences that are at least 80% identical to the comparator sequence.

In the context of the present disclosure, "transcript" refers to a polynucleotide template for a polypeptide. A transcript may comprise RNA (e.g., ssRNA), a cap or cap analog, and/or a polyA tail. A transcript may be capable of translation in a cell (e.g., a bacterial cell and/or a yeast cell). For example, a transcript may be or comprise mRNA. A fusion transcript may comprise polynucleotide templates for two or more polypeptides in a single polynucleotide.

In the context of the present disclosure, "uncapped" refers to a condition of an RNA in which it does not have a cap structure at its 5' end. Uncapped RNA typically has a tri-phosphoryl, di-phosphoryl, mono-phosphoryl or a hydroxyl group at the 5' end.

All publications, patents, and patent applications mentioned in this specification are herein incorporated by reference to the same extent as if each individual publication, patent, or patent application was specifically and individually indicated to be incorporated by reference. All reagents referenced, if unavailable elsewhere, may be obtained from the indicated source and/or New England Biolabs, Inc. (Ipswich, Mass.).

Production of stable mRNA capable of efficient translation upon introduction to a subject may require an appropriate cap structure. In addition, a cap may avoid triggering the innate immune response observed upon introduction of uncapped (5'-triphosphate) RNAs (Pichlmair, et al., Science 2006 314: 997-1001; Diamond, et al., Cytokine & Growth Factor Reviews, 2014 25: 543-550). As such, it may be desirable to add a cap to synthetic RNA in many therapeutic applications (e.g., protein replacement therapy as well as prophylactic or therapeutic vaccination).

Vaccinia virus, like most viruses, has a robust set of mechanisms to co-opt host cell machinery for the production of viral proteins. One such tool is the vaccinia capping enzyme, which forms a Cap 0 structure (m7Gppp5 N) at the 5' end of uncapped RNA molecules through its RNA triphosphatase, guanylyltransferase, and guanine methyltransferase activities. In cells, capping viral transcripts allows them to be transcribed by the infected cells. Other transcripts may be capped rapidly in vitro in the presence of the vaccinia capping enzyme, reaction buffer, GTP, and the methyl donor, SAM. Production of active vaccinia capping enzyme for cell-free vaccine production can be challenging. Properties of VCE may impede production (e.g., high capacity production) and use of the enzyme. For example, efforts to express the vaccinia virus D1R gene in bacteria and yeast as a means to produce and recover the 97 kDa subunit result in poor yields, possibly due, at least in part, to the insolubility and/or hydrophobicity of the 97 kDa subunit. In addition, in vitro assembly of the small and large subunits into a whole protein may yield an enzyme with little to no catalytic activity. Separately produced subunits may not be present in an appropriate ratio or conformation to efficiently or productively bind to one another and/or bind to substrates. Accordingly, a need has arisen for alternatives to VCE for efficient enzymatic capping or RNA molecules.

The present disclosure relates to RNA capping enzymes from Faustovirus and variants thereof (e.g., variants across strains of Faustovirus and variants from related viruses) and kits including these enzymes. The present disclosure further relates to methods of making and using such enzymes. For example, the present disclosure provides FCE and variants thereof. An FCE variant may comprise a non-naturally occurring amino acid sequence that is at least 90% identical (e.g., at least 92% identical, at least 94% identical, at least 96% identical, at least 98% identical) to positions 1-878 of SEQ ID NO: 1 or at least 90% identical (e.g., at least 92% identical, at least 94% identical, at least 96% identical, at least 98% identical) to SEQ ID NO: 1 or at least 90% identical (e.g., at least 92% identical, at least 94% identical, at least 96% identical, at least 98% identical) to positions 389 to 1266 of SEQ ID NO: 2 or at least 90% identical (e.g., at least 92% identical, at least 94% identical, at least 96% identical, at least 98% identical) to SEQ ID NO: 2. An FCE variant may be fused to one or more peptides (e.g., sorting signals, His, MBP or other purification tags) or polypeptides (e.g., other enzymes, linkers or spacers). In some embodiments, an FCE variant may be immobilized, for example, to a solid support (e.g., magnetic, agarose, polystyrene, polyacrylamide, chitin).

In some embodiments, a composition may include one or more FCE variants, one or more substrates of the one or more FCE variants (e.g., uncapped RNA, GDP), one or more intermediates or products (e.g., inorganic phosphate, inorganic diphosphate) of the one or more FCE variants, one or more transcripts of one or more FCE variants (e.g., a capped FCE variant transcript), and any combination thereof. A composition may include, according to some embodiments, an FCE variant and one or more additional components that support storage, transportation, activity and/or use of such FCE variant. For example, a composition may comprise an FCE variant and an uncapped ribonucleic acid (e.g., an uncapped therapeutic RNA), dNTPs, rNTPs, primers, other enzymes (e.g., decapping enzymes, polymerases, or other enzymes), buffering agents (e.g., a storage buffer, a reaction buffer), or combinations thereof.

Uncapped RNA may be synthesized using solid-phase oligonucleotide synthesis chemistry or by transcribing a DNA template using a polymerase (e.g., a bacteriophage polymerase) in an in vitro transcription reaction, for example. In some embodiments, a composition may comprise SAM and/or a cap 2'O methyltransferase enzyme (2'OMTase).

A composition may comprise one or more additives (e.g., glycerol), salts (e.g. KCl), reducing agents, chelating agents (e.g., EDTA), detergents, and/or denaturants (e.g., caffeine, urea), among others. A composition comprising dNTPs may include one, two, three or all four of dATP, dTTP, dGTP and dCTP. A composition comprising rNTPs may include one, two, three of all four or rATP, rUTP, rGTP and rCTP. A composition may further comprise one or more modified nucleotides. A composition may comprise one or more modified nucleotides.

A composition may optionally comprise one or more primers (random primers, bump primers, exonuclease-resistant primers, chemically-modified primers, custom sequence primers, or combinations thereof). Compositions optionally may comprise one or more of the components set forth below for kits. In some embodiments, a composition may be glycerol-free, may be dry (e.g., as a result of lyophilization), and/or may be aqueous.

A composition may be formulated for delivery to a subject (e.g., a human subject, a non-human animal subject). A composition, for example, a composition including one or more products of an FCE variant, may be free of materials (e.g., enzymes) derived from non-human animals according to some embodiments.

Methods

According to some embodiments, a capping method may comprise contacting a single-chain RNA capping enzyme (e.g., FCE, an FCE variant) with one or more of a target RNA (e.g., an uncapped therapeutic RNA), an NTP, a modified NTP, a cap, S-adenosylmethionine (SAM), and a buffering agent to form a reaction mix. This contact may be at a sufficient temperature and for a sufficient time to form a capped target RNA. For example, the contact may be at a temperature (e.g., constant or varying) in the range of 37° C.-60° C. and/or for a time in the range of seconds to hours (e.g., from 60 seconds to 16 hours). The contacting may be RNase free and/or may further include contacting the other components with an RNase inhibitor. The contacting may further comprise contacting the other components with a cap 2'O methyltransferase enzyme (2'OMTase).

A single-chain RNA capping enzyme for a capping method may comprise an amino acid sequence that is at least 90% identical (e.g., at least 92% identical, at least 94% identical, at least 96% identical, at least 98% identical) to positions 1-878 of SEQ ID NO: 1 or at least 90% identical (e.g., at least 92% identical, at least 94% identical, at least 96% identical, at least 98% identical) to positions SEQ ID NO: 1 or at least 90% identical (e.g., at least 92% identical, at least 94% identical, at least 96% identical, at least 98% identical) to positions 389 to 1266 of SEQ ID NO: 2 or at least 90% identical (e.g., at least 92% identical, at least 94% identical, at least 96% identical, at least 98% identical) to SEQ ID NO: 2. A capping method may further comprise monitoring the appearance capped target RNA. Capped RNA may be monitored/detected by denaturing urea polyacrylamide gel electrophoresis, radiometric assays, capillary electrophoresis, or mass spectrometry-based methods (e.g., as provided by Beverly, M., Dell, A., Parmar, P., and Houghton, L. 2016. Label-free analysis of mRNA capping efficiency using RNase H probes and LC-MS. *Analytical and bioanalytical chemistry* 408:5021-5030).

A capping method, in some embodiments, may comprise (a) contacting a polymerase with one or more of a polynucleotide template (DNA or RNA) encoding a target RNA, rNTPs and/or modified rNTPs, and a buffer to form a transcription product comprising the target RNA and (b) contacting a single-chain RNA capping enzyme (e.g., FCE, an FCE variant) with one or more of the transcription products, an NTP, a modified NTP, a cap, S-adenosylmethionine (SAM), and a buffering agent to form a reaction mix. This contact may be at a sufficient temperature and for a sufficient time to form a capped target RNA. For example, the contact may be at a temperature (e.g., constant or varying) in the range of 37° C.-60° C. and/or for a time in the range of second to hours (e.g., from 60 seconds to 16 hours).

A capping method may further comprise contacting the capped RNA with a one or more pharmaceutically acceptable additives (e.g., excipients, diluents, and/or carriers), including, for example, fluids, solvents, dispersion media, wetting agents, crowding agents, micelles, lipidoids, liposomes, polymers, lipoplexes, peptides, proteins, salts, surface active agents, isotonic agents, thickeners, emulsifiers, preservatives, stabilizers, solubilizers, buffers, sugars, starches, cellulose, waxes, glycols, polyols, polyesters, polycarbonates, polyanhydrides, hyaluronidase, nanoparticles (e.g., lipid nanoparticles, core-shell nanoparticles, and/or nanoparticle mimics), and combinations thereof. In some embodiments, pharmaceutically acceptable additives protect, preserve, and/or stabilize a capped RNA during manufacture, storage, and/or administration to a subject. Examples of pharmaceutical acceptable additives include those described in U.S. Patent Publication No. 2017/0119740. A capping method may further comprise contacting the capped RNA with one or more additives selected from lipidoids, liposomes, polymers, lipoplexes, peptides, proteins, cells transfected with HCMV RNA vaccines (e.g., for transplantation into a subject), hyaluronidase, nanoparticles (e.g., lipid nanoparticles, core-shell nanoparticles, and/or nanoparticle mimics).

Capped RNAs may be formulated for delivery and/or delivered to a eukaryotic organism. Examples of subjects that may receive a capped RNA include humans and non-human animals (e.g., mouse, rat, rabbit, dog, cat, cattle, swine, sheep, horse or primate). Capped RNAs may be delivered to plants or plant cells, according to some embodiments, to confer or augment resistance to or tolerance of an environmental condition (e.g., drought, salt) and/or to prevent, mitigate or treat herbivory, pathogen infection, or the effects thereof. Capped RNA also may be delivered to one or more yeast cells.

In some embodiments, the present disclosure provides methods for preparing a capped RNA dosage form comprising, contacting an uncapped RNA with an FCE variant to form a capped RNA, and contacting the capped RNA with one or more pharmaceutically acceptable additives, binders, buffers, coatings, colors, controlled release agents, delivery agents (e.g., liposomes, propellants), diluents, disintegrants, dyes, excipients, fillers, lipids, lubricants, salts, sorbants, stabilizers, and/or other agents to produce an RNA dosage form. A capped RNA may be combined (e.g., in a single dosage form or delivered concurrently or in sequence with one or more other active pharmaceutical agents. A capped RNA and/or its encoded translation product(s) may function in a subject as an active pharmaceutical agent, according to some embodiments. A capped RNA (e.g., a capped RNA dosage form) may be administered by any suitable route of administration, including transdermal, oral, enteral, parenteral, ocular, ottic, transmucosal, sublingual, and pulmonary (e.g., by nebulization and/or inhalation) routes, and combinations thereof.

Capped RNA can either be naked or formulated in a suitable form for delivery to a subject, e.g., a human. Formulations can include liquid formulations (solutions, suspensions, dispersions), topical formulations (gels, ointments, drops, creams), liposomal formulations (such as those described in: U.S. Pat. No. 9,629,804 B2; US 2012/0251618 A1; WO 2014/152211; US 2016/0038432 A1). The cells into which the RNA product is introduced may be in vitro (i.e., cells that have been cultured in vitro on a synthetic medium). Accordingly, the RNA product may be transfected into the cells. The cells into which the RNA product is introduced may be in vivo (cells that are part of a mammal). The cells into which the RNA product is introduced may be present ex vivo (cells that are part of a tissue, e.g., a soft tissue that has been removed from a mammal or isolated from the blood of a mammal).

Methods for production of an FCE variant may comprise, for example, contacting a polynucleotide encoding such FCE variant with an expression system (e.g., a bacterial expression system, a yeast expression system, an insect expression system, a mammalian expression system, a viral expression system or a cell-free expression system). A method of producing an FCE variant may comprise contacting an uncapped FCE variant transcript with a capping enzyme (e.g., vaccinia capping enzyme, FCE, an FCE variant) to form a capped FCE variant transcript. A method may further include contacting a capped FCE variant transcript with an expression system to form FCE protein.

An FCE variant protein may be produced, according to some embodiments, by constructing an expression plasmid compatible to E. coli or yeast expression systems under the control of an appropriate promoter. The plasmid can be introduced into the cells via transformation and the resultant E. coli or yeast strain can be cultured using appropriate methods. The expression of the FCE variant protein can be induced by subjecting the culture to appropriate conditions in case of inducible promoters or by following appropriate culture conditions for auto-induced promoters. Cultivation conditions (e.g., time, temperature, media composition) may be maintained or adjusted as needed to express the FCE protein variant. Cultures may be harvested, for example, by centrifugation or tangential flow filtration. Harvested cells (e.g., in the form of pellets) may be stored at low temperatures or lysed using an appropriate method such as sonication or mechanical sheering. Lysates may be clarified, for example, by centrifugation or tangential flow filtration. The FCE variant protein may be purified from the clarified lysate or spent culture medium, for example, by chromatographic methods.

In some embodiments, an FCE variant protein may be produced by contacting an FCE variant protein expression DNA construct operably linked to an expression control sequence (e.g., an appropriate promoter) to an in vitro transcription/translation system such as PURExpress In vitro Protein Synthesis Kit (New England Biolabs, Inc.) or TnT Quick Coupled Transcription/Translation System (Promega). In addition, an FCE variant protein can be produced by contacting an FCE variant protein expression DNA construct under the control of an appropriate promoter to a cell-free protein synthesis system derived from organisms such as E. coli (e.g., NEBExpress Cell-free E. coli Protein Synthesis System (New England Biolabs, Inc.), rabbit, wheat germ, insect, or human. Reaction conditions (e.g., time, temperature, reaction composition) may be maintained or adjusted as needed to express the FCE protein variant. Expressed variant protein may be purified by appropriate methods (e.g., chromatographic methods).

Kits

The present disclosure further relates to kits including an FCE variant. For example, a kit may include an FCE variant and an uncapped ribonucleic acid, dNTPs, rNTPs, primers, other enzymes (e.g., decapping enzymes, polymerases, or other enzymes), buffering agents, or combinations thereof. An FCE variant may be included in a storage buffer (e.g., comprising glycerol and a buffering agent). A kit may include a reaction buffer which may be in concentrated form, and the buffer may contain additives (e.g. glycerol), salt (e.g. KCl), reducing agent, EDTA or detergents, among others. A kit comprising dNTPs may include one, two, three or all four of dATP, dTTP, dGTP and dCTP. A kit comprising rNTPs may include one, two, three of all four or rATP, rUTP, rGTP and rCTP. A kit may further comprise one or more modified nucleotides. A kit may optionally comprise one or more primers (random primers, bump primers, exonuclease-resistant primers, chemically-modified primers, custom sequence primers, or combinations thereof). One or more components of a kit may be included in one container for a single step reaction, or one or more components may be contained in one container, but separated from other components for sequential use or parallel use. The contents of a kit may be formulated for use in a desired method or process.

A kit is provided that contains: (i) an FCE variant; and (ii) a buffer. An FCE variant may have a lyophilized form or may be included in a buffer (e.g., a storage buffer or a reaction buffer in concentrated form). A kit may contain an FCE variant in a mastermix suitable for receiving and capping a template ribonucleic acid. An FCE variant may be a purified enzyme so as to contain no other detectable enzyme activities. The reaction buffer in (ii) and/or storage buffers containing an FCE variant in (i) may include non-ionic, ionic e.g. anionic or zwitterionic surfactants, denaturants, and/or crowding agents. A kit may include an FCE variant and the reaction buffer in a single tube or in different tubes.

A subject kit may further include instructions for using the components of the kit to practice a desired method. The instructions may be recorded on a suitable recording medium. For example, instructions may be printed on a substrate, such as paper or plastic, etc. As such, the instructions may be present in the kits as a package insert, in the labeling of the container of the kit or components thereof (i.e., associated with the packaging or sub-packaging) etc. Instructions may be present as an electronic storage data file residing on a suitable computer readable storage medium (e.g., a CD-ROM, a flash drive). Instructions may be provided remotely using, for example, cloud or internet resources with a link or other access instructions provided in or with a kit.

EXAMPLES

Some specific example embodiments may be illustrated by one or more of the examples provided herein.

Example 1: Plasmids and Expression Cassettes

Example 1A. Construction of *P. pastoris* FCE Expression Vectors for Secreted Expression The gene encoding the mRNA capping enzyme, FCE containing a C-terminal 8× Histidine tag, was amplified by PCR using the forward and reverse primers, respectively:

```
                                         (SEQ ID NO: 3)
5'agaaaagagaggccgaagctGCGAAGCGTCTGCAGCGT,
and (SEQ ID NO: 4)
5'cctcttgagcggccgccctTTAGTGGTGGTGGTGGTGG.
```

The forward and reverse primers were engineered to contain sequences that overlap the pD912(GAP) vector (lower case) (FIG. 1A). The NEBuilder Assembly Tool was used for primer and assembly design. The 2661 bp FCE gene was amplified from the plasmid pFCE-CHis8 containing the full-length gene and 8× Histidine tag, using Q5 High-Fidelity 2× Master Mix (New England Biolabs). The pD912 (GAP) was prepared from pD912(AOX) vector by replacing 462 bp long AOX1 promoter sequence with 483 bp long DNA fragment containing *Pichia pastoris* GAP promoter. The 3826 bp vector fragment was amplified from the plasmid pD912(GAP) by PCR using the forward and reverse primers, respectively:

```
                                         (SEQ ID NO: 5)
5'AGGGGCGGCCGCTCAAGA,
and (SEQ ID NO: 6)
5'AGCTTCGGCCTCTCTTTTC.
```

This integrative expression vector contains the mating factor alpha secretion leader for extracellular expression, the GAP1 promoter which initiates and terminates transcription and the zeocin resistance gene which allows for selection of transformants by growth on zeocin-containing medium. The two fragments were joined using NEBuilder HiFi DNA Assembly Master Mix (New England Biolabs). 2 µl of the reaction was transformed into 50 µl of NEB 5-alpha Competent *E. coli* (High Efficiency) cells, plated on LB-zeocin (25 µg/mL) plates and incubated overnight at 37° C. resulting in a *P. pastoris* expression vector pD912(GAP)-FCE (WT)-8His (SEQ ID NO:1) (FIG. 2).

For the construction of asparagine-linked (N-linked) glycan variants of FCE, the potential N-linked glycosylation sites were first identified using the NetNGlyc 1.0 server (www.cbs.dtu.dk/services/NetNGlyc/). The prediction results indicated 5 potential sites at amino acid sequence positions 215, 337, 572, 648, and 833. Positions 215, 337 and 572 scored above the N-glycosylation threshold potential. In light of these predictions, 2 variant constructs were generated, one with N215Q, N337Q, N572Q, N648Q, and N833Q substitutions, and the other with N215Q, N337Q and N572Q substitutions. The Q5 Site Directed Mutagenesis Kit (New England Biolabs, Inc.) was used for construction of the variant expression vectors. The NEBaseChanger tool was used for primer design. The primers for each variant are listed below:

| Name | Sequence | SEQ ID NO |
|---|---|---|
| N215Q-Fwd | 5'TCGTAACGCGcaaAGCACCGCGG | 7 |
| N215Q-Rev | 5'ACGCTGCTCAGCAGCTCCAC | 8 |
| N337Q-Fwd | 5'TATCATTAGCcaaAACACCCAGGTTTATAC | 9 |
| N337Q-Rev | 5'ACGTCGAACACGTACAGA | 10 |
| N572Q-Fwd | 5'CTTCGAGAAGcaaAAAAGCGATATCTATG | 11 |
| N572Q-Rev | 5'TAGCCCGGGTTATACTTG | 12 |
| N648Q-Fwd: | 5'ACCGGCTACcaaAAGAGCCACCGTGGCGGT | 13 |
| N648Q-Rev: | 5'GTGGCTCTTTTGGTAGCCGGTAATCTCGTT | 14 |
| N833Q-Fwd: | 5'GAAAGCGCGcaaTTCAGCGTGCTGTACGAG | 15 |
| N833Q-Rev: | 5'CACGCTGAATTGCGCGCTTTCAACCAGATC | 16 |

The forward primers contained the nucleotide sequence encoding the glutamine residue (lower case). The FCE gene containing a single mutated N-linked site was amplified from the plasmid pD912(GAP)-FCE-8His using Q5 High-Fidelity 2× Master Mix (New England Biolabs). The pD912 ($P_{GAP}$) vector fragment, containing the *S. cerevisae* α-mating factor pre-pro signal sequence, was also amplified by Q5 High-Fidelity 2× Master Mix using the primers described above. Each FCE fragment was joined to the pD912 (GAP) vector fragment using NEBuilder HiFi DNA Assembly Master Mix. This resulted in the three plasmids, pD912 (GAP)-FCE(N215Q)-8His, pD912(GAP)-FCE(N337Q)-8His and pD912(GAP)-FCE (N572Q)-8His. All plasmids were sequence verified to contain the correct mutations.

A plasmid containing three N-glycan variants was created by amplifying the 708 bp fragment from N337 to N572 and assembling the resulting PCR product into the pD912 (GAP)-FCE(N215Q)-8His plasmid using NEBuilder HiFi DNA Assembly Mix. This resulted in the plasmid, pD912 (GAP)-FCE(N215Q/N337Q/N572Q)-8His (SEQ ID NO:24).

A plasmid containing all five N-glycan variants was created by amplifying the 557 bp fragment from N648 to N833 and assembling the resulting PCR product into the pD912(GAP)-FCE(N215Q/N337Q/N572Q)-8His plasmid using NEBuilder HiFi DNA Assembly Mix. This resulted in the plasmid, pD912(GAP)-FCE(N215Q/N337Q/N572Q/N648Q/N833Q)-8His (SEQ ID NO:24).

Double variants of N215Q/N337Q and N215Q/N572Q were constructed using the Q5 Site Directed Mutagenesis Kit as described above resulting in the plasmids, pD912 (GAP)-FCE(N215Q/N337Q)-8His and pD912(GAP)-FCE (N215Q/N572Q)-8His.

Example 1B. Construction of *K. lactis* FCE Expression Vectors for Cytoplasmic Expression The gene encoding the mRNA capping enzyme, FCE containing a C-terminal 8× Histidine tag, was amplified by PCR using the forward and reverse primers, respectively:

(SEQ ID NO: 17)
5'tcggggatgacgatgacaagGCGAAGCGTCTGCAGCGT
and (SEQ ID NO: 18)
5'tcagcctctctttctcgagTTAGTGGTGGTGGTGGTGG.

Figure 1B:
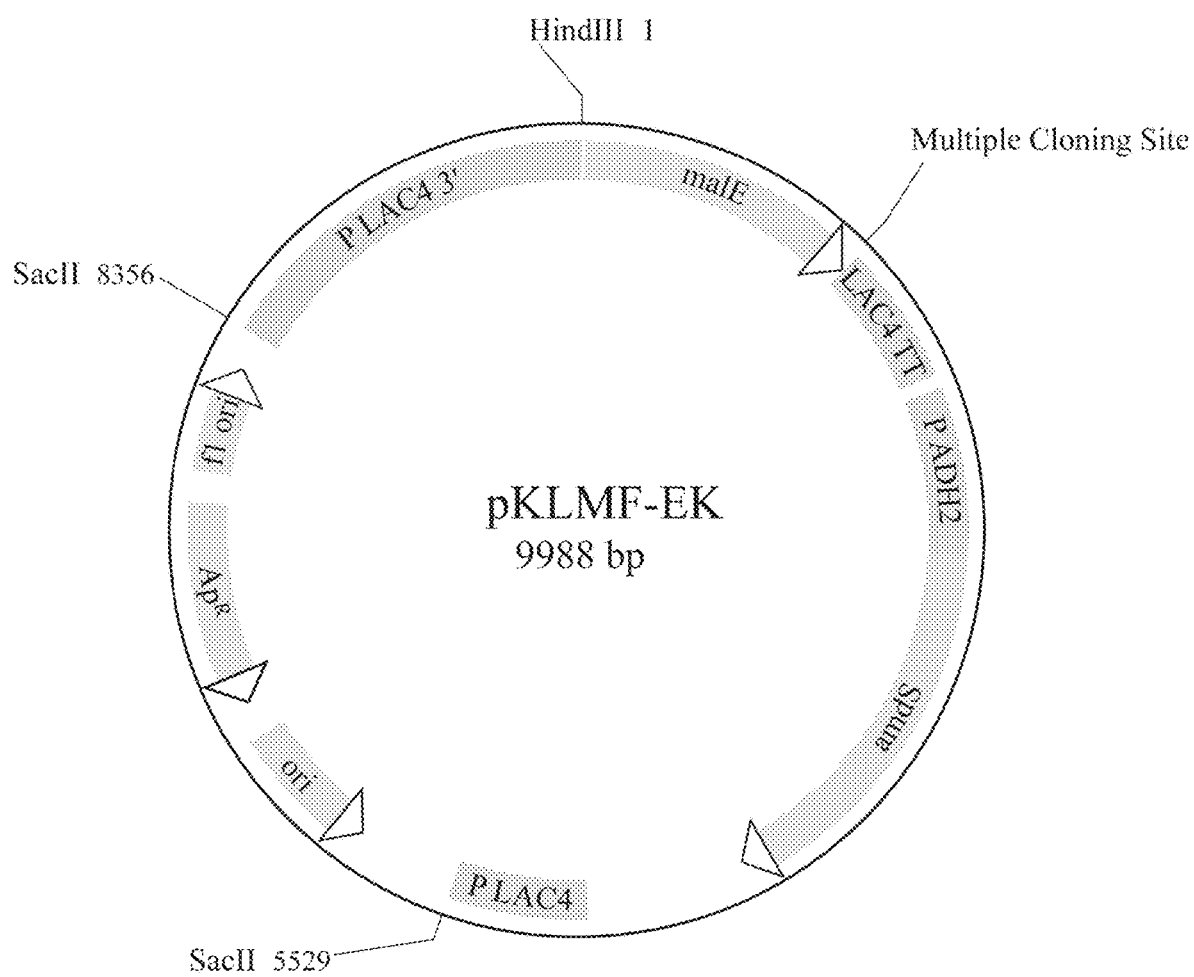

The forward and reverse primers were engineered to contain sequences that overlap the pKLMF-EK vector (New England Biolabs) (lower case) (FIG. 1B). The NEBuilder Assembly Tool was used for primer and assembly design. The 2661 bp FCE gene was amplified from the plasmid pFCE-CHis8 (Siuhong Chan) containing the full-length gene and 8× Histidine tag, using Q5 High-Fidelity 2× Master Mix (New England Biolabs).

The 10028 bp vector fragment was amplified from the plasmid (CT867) pKLMF-A313V-EK-LongerLinker (unoptimized) by Q5 High-Fidelity 2× Master Mix using the forward and reverse primers, respectively:

(SEQ ID NO: 19)
5'CTCGAGAAAAGAGAGGCTGAAGCT
and (SEQ ID NO: 20)
5'CTTGTCATCGTCATCCCCGAG.

This integrative expression vector contains the malE gene which encodes for maltose binding protein (MBP), the LAC4 promoter which initiates and terminates transcription and the acetamidase gene which allows for selection of transformants by growth on acetamide-containing medium. In this vector, *K. lactis* α-mating factor pre-pro signal sequence has been replaced with the malE gene. Thus MBP-fusion proteins will not be directed to the secretory pathway but instead will be retained in the yeast cytosol. The two fragments were joined using NEBuilder HiFi DNA Assembly Master Mix (New England Biolabs). The assembled linear expression cassette (FIG. 2) was amplified by PCR using the forward and reverse primers, respectively (SEQ ID NO:2):

(SEQ ID NO: 21)
5'GATCGACTCATAAAATAGTAACC
and (SEQ ID NO: 22)
5'CCGCGGAAATTTAGGAATTTTAAAC.

Example 2: Yeast Transformation and Expression

*Pichia pastoris* aox1Δ (MutS) (ATUM, formerly DNA 2.0) and *Kluyveromyces lactis* GG799 (New England Biolabs) strains were for each relevant experiment. Electrocompetent cells were prepared using the lithium acetate/DTT method (Wu and Letchworth, 2004). Electroporation conditions were 1.5 KV, 25 µF and 200 Ohm using a 0.2 cm cuvette followed by selection of transformants by growth on yeast peptone dextrose (YPD) agar medium supplemented with 1 M sorbitol and 500 µg/mL Zeocin (Teknova) (*P. pastoris*) and yeast carbon base (YCB) supplemented with 5 mM acetamide (*K. lactis*) and incubated for 3-4 days at 30° C.

Three micrograms *P. pastoris* expression plasmids were linearized by SacI-HF restriction digestion and the purified products were used to transform electrocompetent *P. pastoris* MutS cells. 0.5 µg purified *K. lactis* linear expression cassette generated by PCR, was used to transform electrocompetent *K. lactis* GG799 cells.

Eight to twelve transformants were patched onto fresh selection plates and incubated for an additional 1-2 days at 30° C. For the identification of transformants by PCR, genomic DNA was isolated from each strain using lithium acetate/sodium dodecyl sulfate (LiOAc/SDS) method (Lööke et al., 2011). PCR was used to identify transformants having an integrated expression cassette.

Example 3: Yeast Culture Conditions and Expression

For *Pichia pastoris* constructs (containing GAP promoter), transformants were grown at 30° C. in 5 mL of BMGY-Buffered Glycerol Complex Medium (Teknova) (1% yeast extract, 2% tryptone, 1.34% yeast nitrogen base (YNB) without amino acids with ammonium sulfate, 0.0004% biotin, 1% glycerol as the carbon source, 100 mM potassium phosphate, pH 6.0). After 48 hours, the spent culture media was harvested.

For *Kluyveromyces lactis* constructs (containing LAC4 promoter), transformants were grown at 30° C. in 5 mL of yeast medium (1% yeast extract, 2% peptone) supplemented with 2% galactose as the carbon source. After 48 hours, the cells were harvested.

Example 4: Analysis of Cultures

The spent culture media (*P. pastoris* constructs) were buffer-exchanged in 50 mM Tris-HCl, pH 7.5 buffer containing 300 mM NaCl and concentrated ten-fold using Vivaspin 30 kDa MWCO filters (Sartorius). To assess the extent of glycosylation, the concentrated spent culture media were subject to Endo Hf (New England Biolabs) digestions under native conditions in the presence of 1× GlycoBuffer 3 (50 mM sodium acetate, pH 6.0).

FCE proteins (wild-type and N-glycan variants) were purified from the concentrated spent cultures using NEB-Express Ni Spin Columns (New England Biolabs). The columns were washed twice with 50 mM Tris-HCl, pH 7.5 buffer containing 300 mM NaCl and 5 mM imidazole then once with 50 mM Tris-HCl, pH 7.5 buffer containing 300 mM NaCl and 10 mM imidazole. The purified protein was eluted with 50 mM Tris-HCl, pH 7.5 buffer containing 300 mM NaCl and 500 mM imidazole.

To prepare cell lysates (*K. lactis* constructs), cells were resuspended in 50 mM Tris-HCl, pH 7.5 buffer containing 300 mM NaCl and sonicated (Qsonica). The soluble cell lysate was pre-cleared by centrifugation at 16000×g for 15 minutes at 4° C. The cell lysates and spent culture media were analyzed by SDS-PAGE on 4-20% polyacrylamide gel, followed by western blotting with a His-tag antibody (Thermo Fisher Scientific).

Example 5: In Vitro mRNA Capping Assay

In vitro capping reactions were carried out in a 10 μL reaction containing 1× capping buffer (50 mM Tris pH 8.0, 5 mM KCl, 1 mM MgCl$_2$, 1 mM DTT) supplemented with 0.1 mM S-adenosylmethionine, 0.5 mM GTP, 500 nM substrate RNA (SEQ ID NO: 23: 5'-GUAGAACUUCGU-CGAGUACGCUCAA[FAM]-3', Bio-Synthesis, Inc.), and spent culture medium of cell lysate at 37° C. for 30 minutes. Reactions were stopped by adding 10 μL of quenching solution (20 mM EDTA, 2% SDS). Reactions were diluted in nuclease-free water to reach a final substrate concentration of 5 nM before capillary electrophoresis on either an Applied Biosystems 3130xl Genetic Analyzer (16 capillary array) or an Applied Biosystems 3730xl Genetic Analyzer (96 capillary array) using GeneScan 120 LIZ dye Size Standard (Applied Biosystems). Reaction products were analyzed using PeakScanner software (Thermo Fisher Scientific).

Example 6: Production of Glycosylated FCE

Figure 3A:
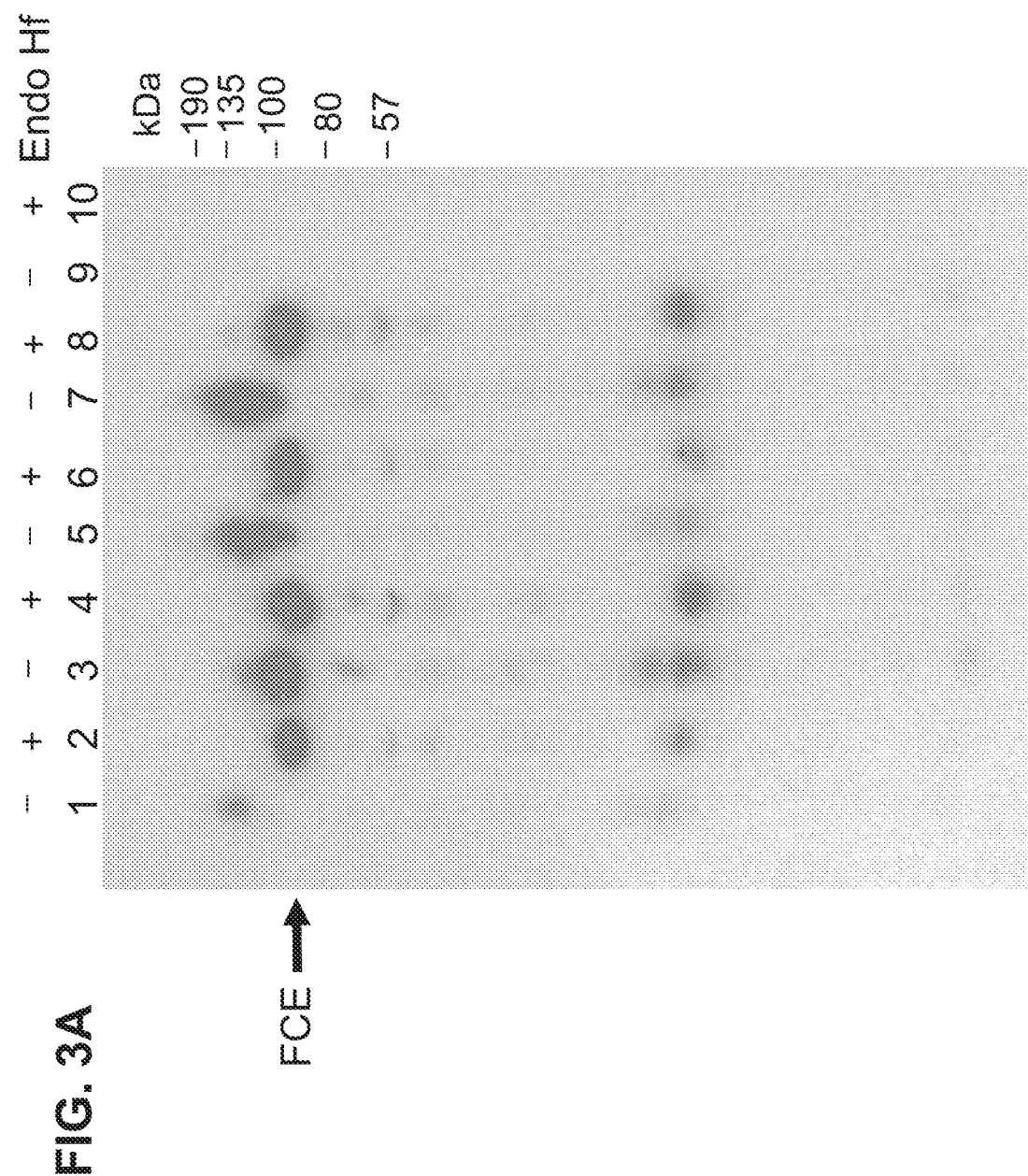
FIGS. 3A and 3B show effective expression of FCE constructs in Pichia pastoris and Kluyveromyces lactis.

Western blot analysis of the transformants expressing FCE indicated that the recombinant fusion protein is secreted in the media from *Pichia pastoris* cells. The results also indicated, that the protein is glycosylated as evidenced by the mobility shift and removal of smears after EndoHf digestion. Variant N215Q shows significant reduction in glycosylation while variants N337Q and N572Q show a slight reduction in glycosylation as compared to wild type (FIG. 3A and FIG. 3B).

Figure 3B:
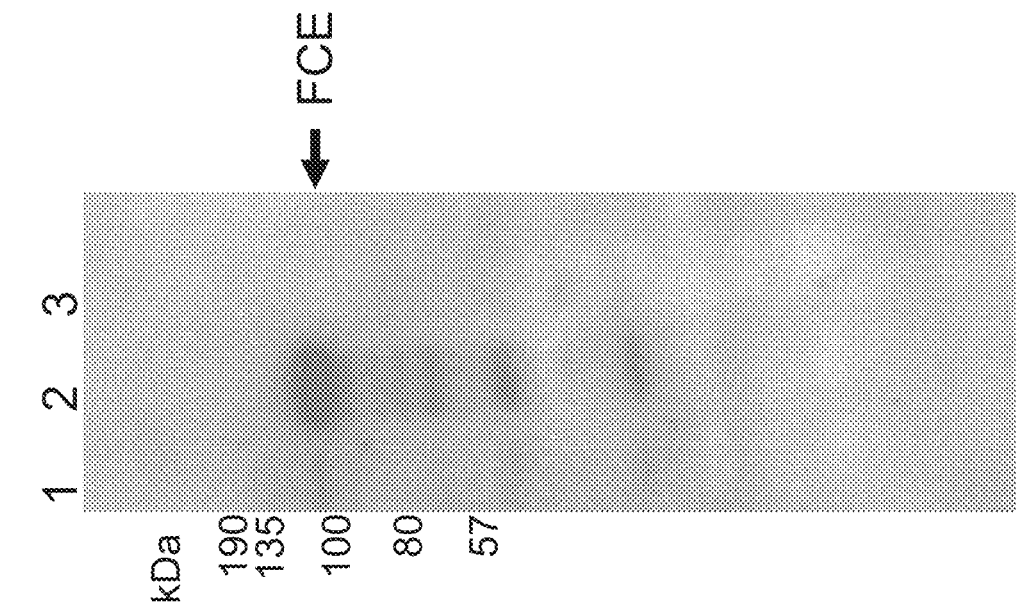
Figure 4A:
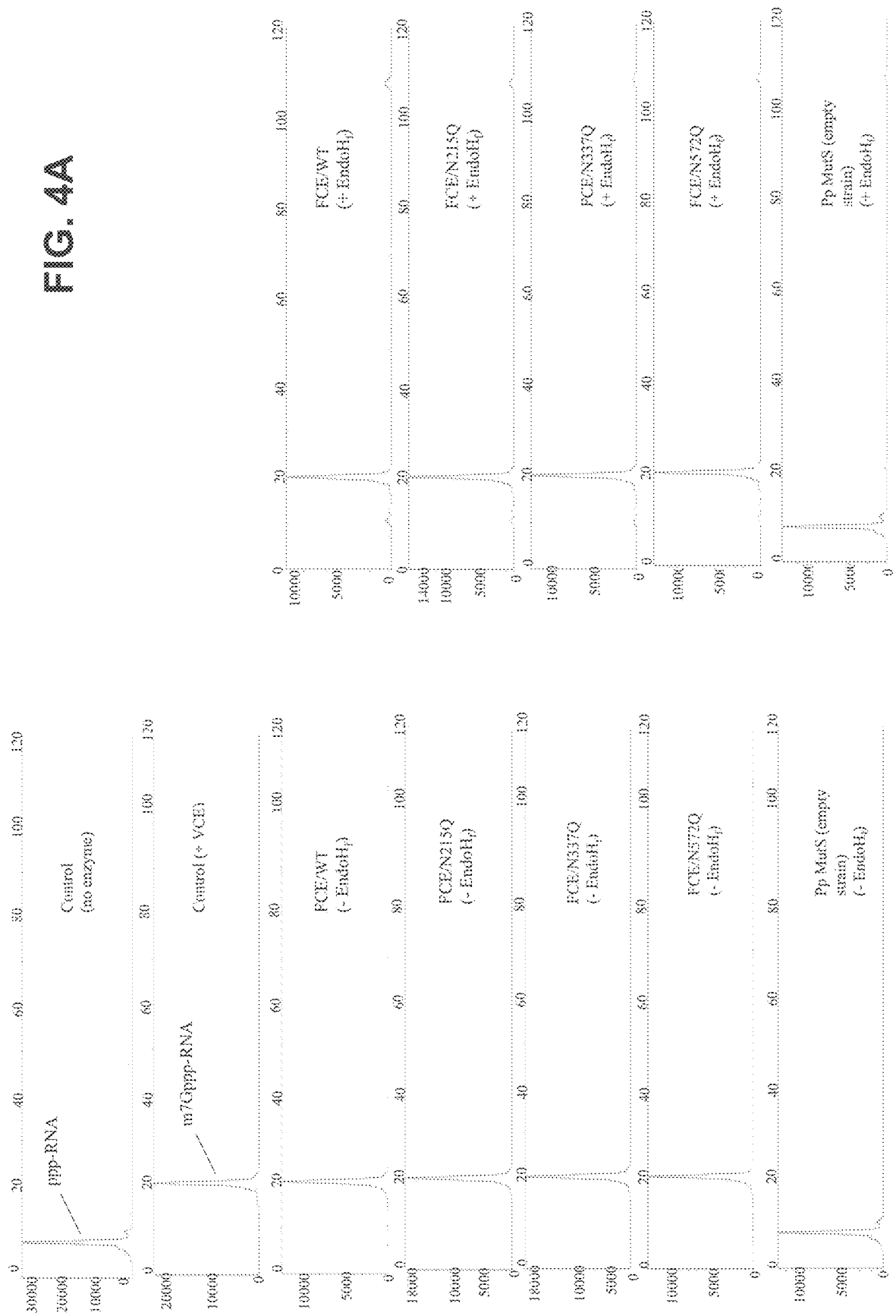

The full-length FCE is also expressed as a single polypeptide in the *K. lactis* cytoplasm (FIG. 3B). All recombinants displayed mRNA capping activity both before and after EndoHf digestion (FIG. 4A and FIG. 4B).

Figure 5:
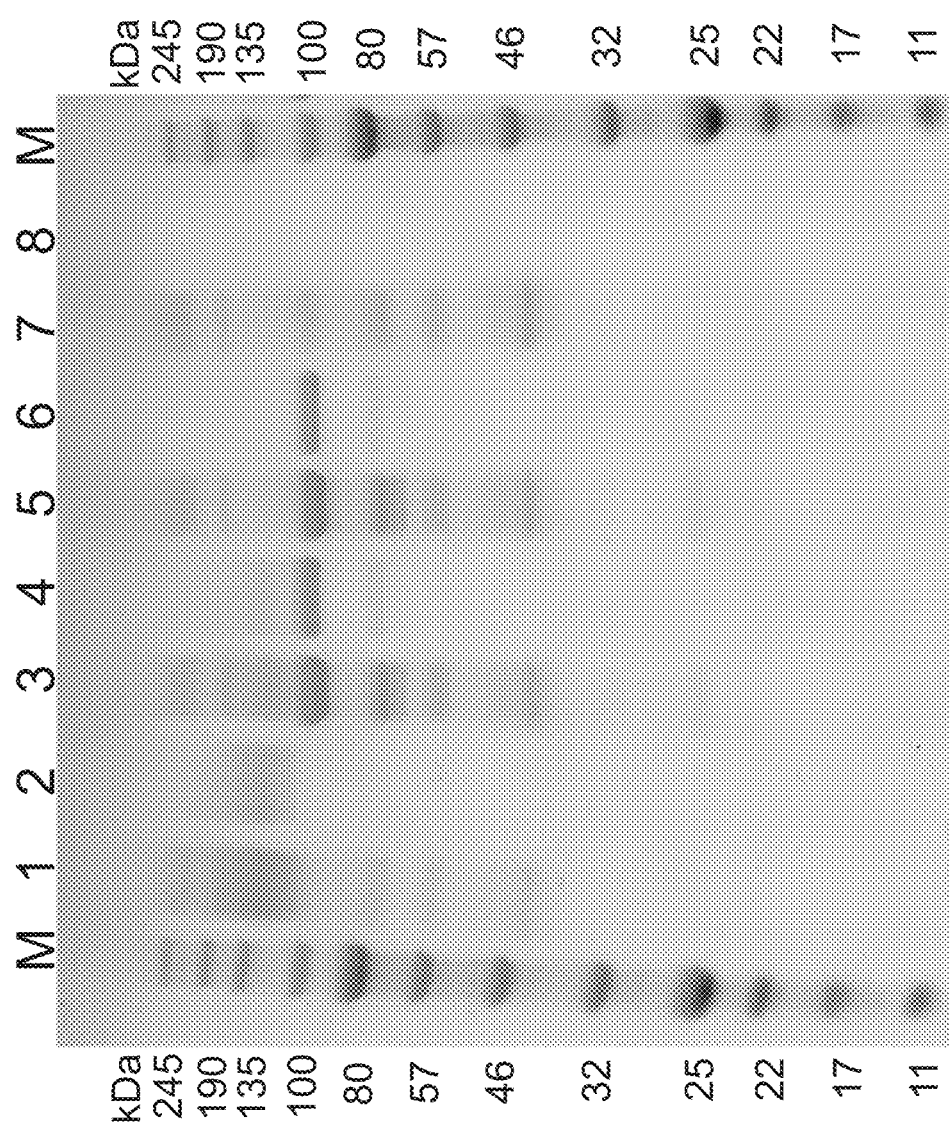
FIG. 5 shows secreted expression of FCE WT, FCE (N215Q/N337Q/N572Q) and FCE (N215Q/N337Q/N572Q/N648Q/N833Q) mutants in *Pichia pastoris* cells transformed with constructs containing the GAP promoter. Transformants were grown in Buffered Minimal Glycerol medium, BMGY with 1% glycerol at 30° C. for 48 hours. Spent culture media were harvested, concentrated, buffer exchanged and purified using NEBExpress Ni Spin Columns. The load (spent culture media) and elution fractions were analyzed by SDS-PAGE on a 4-20% polyacrylamide gel and stained using Simply Blue Safe Stain (Thermofisher) . Lanes 1, 2: spent culture medium and elution fraction of FCE-WT; Lanes 3, 4: spent culture medium and elution fraction of FCE (N215Q/N337Q/N572Q) mutant; Lanes 5, 6: spent culture medium and elution fraction of FCE (N215Q/N337Q/N572Q/N648Q/N833Q) mutant; Lanes 7, 8: spent culture medium and elution fraction of control *P. pastoris* MutS (empty strain); M: Color Prestained Protein Standard, Broad Range (NEB).
Figure 6:
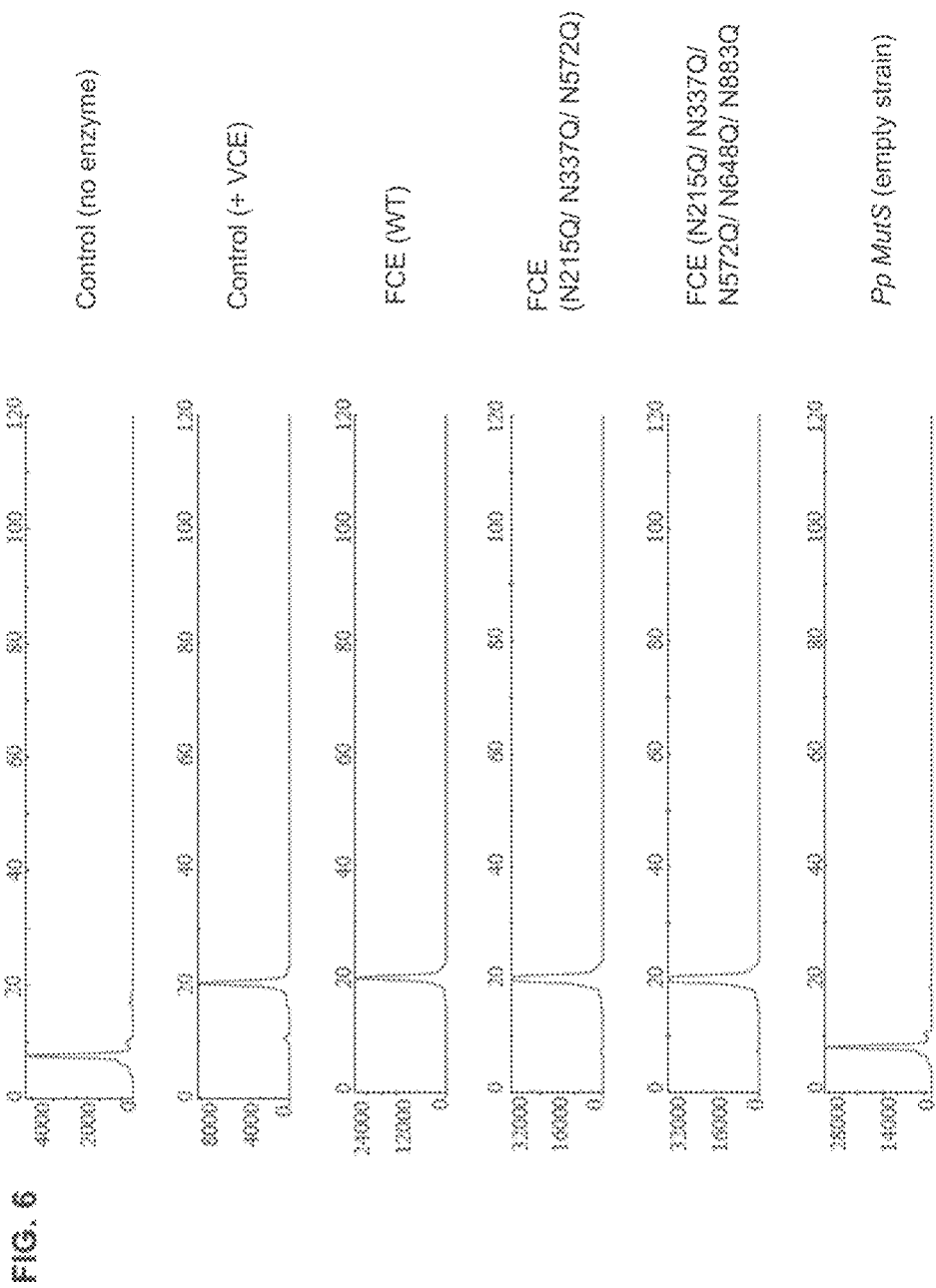
FIG. 6 shows the activity of the concentrated and buffer exchanged spent culture media, from *P. pastoris* cells, of FCE WT, FCE (N215Q/N337Q/N572Q), FCE (N215Q/N337Q/N572Q/N648Q/N833Q) and control *P. pastoris* MutS (empty strain).

After nickel spin column purification of wild type FCE and mutants expressed from *Pichia pastoris* cells, the load (spent culture media) and elution fractions were analyzed by SDS-PAGE. The eluted FCE (N215Q/N337Q/N572Q) mutant shows a significant decrease in glycosylation as observed by the improved band resolution as compared to wild type. The purified FCE (N215Q/N337Q/N572Q/N648Q/N833Q) mutant shows further improved band resolution, indicating a further decrease in glycosylation (FIG. 5). The concentrated spent culture media from all 3 recombinants showed mRNA capping activity (FIG. 6).

Figure 7A:
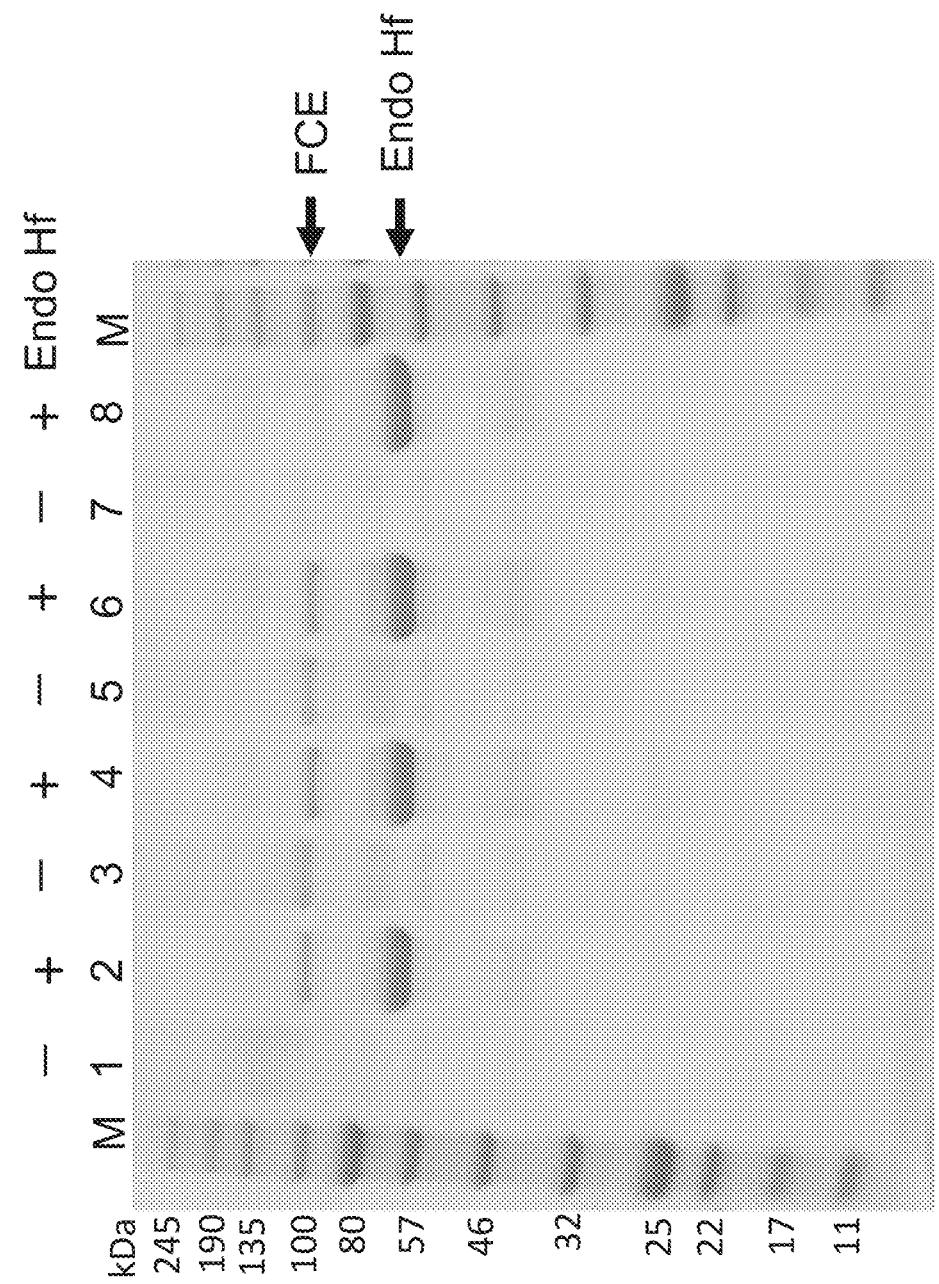
FIG. 7A and FIG. 7B represent the secreted expression of FCE wild type (WT), (N215Q/N337Q/N572Q) and (N215Q/N337Q/N572Q/N648Q/N833Q)N-glycan mutants in *Pichia pastoris* cells transformed with constructs containing GAP promoter and control *P. pastoris* MutS (empty strain). The transformants were grown in Buffered Minimal Glycerol medium, BMGY with 1% glycerol at 30° C. for 48 hours. The spent culture medium was harvested, concentrated and buffer exchanged. After overnight digestion with Endo Hf, the spent medium was analyzed by SDS-PAGE on a 4-20% polyacrylamide gel followed by western blotting with a His-tag antibody. Lanes 1, 2: FCE-WT −/+Endo Hf; Lanes 3, 4: FCE (N215Q/N337Q/N572Q) −/+Endo Hf; Lanes 5, 6: FCE (N215Q/N337Q/N572Q/N648Q/N833Q) −/+Endo Hf; Lanes 7, 8: control *P. pastoris* (empty strain) −/+Endo Hf; M: Color Prestained Protein Standard, Broad Range (NEB).
Figure 7B:
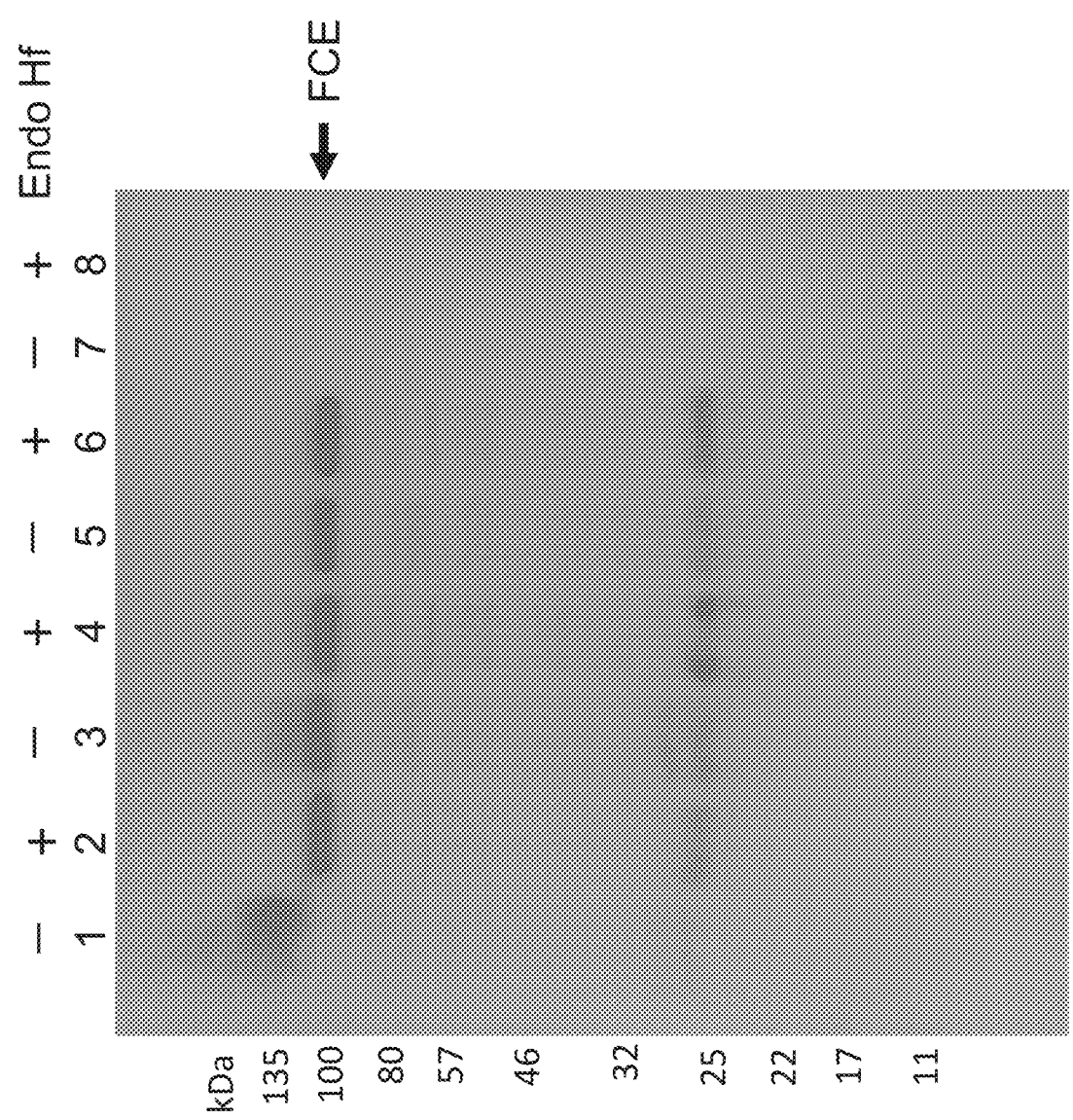

Further SDS-PAGE analysis and Western blot analysis following EndoHf treatment of wild type FCE, FCE (N215Q/N337Q/N572Q) and FCE (N215Q/N337Q/N572Q/N648Q/N833Q) spent culture confirmed the reduction or elimination of glycosylation of the secreted protein (FIG. 7A and FIG. 7B).

REFERENCES

Beverly, M., Dell, A., Parmar, P., and Houghton, L. 2016. Label-free analysis of mRNA capping efficiency using RNase H probes and LC-MS. *Analytical and bioanalytical chemistry* 408:5021-5030.

Diamond, et al., Cytokine & Growth Factor Reviews, 2014 25: 543-550.

Kore, Nucleosides, Nucleotides, and Nucleic Acids, 2006, 25: 15 307-14.

Kore, Nucleosides, Nucleotides, and Nucleic Acids, 2006, 25: 337-40.

Lööke, M., Kristjuhan, K., & Kristjuhan, A. (2011). Extraction of genomic DNA from yeasts for PCR-based applications. *BioTechniques*, 50(5), 325-328.

Pichlmair, et al., Science 2006 314: 997-1001.

Ramanathan, Nucleic Acids Res. 2016 44: 7511-7526.

Sakhtah H, Behler J, Ali-Reynolds A, Causey TB, Vainauskas S, Taron CH. 2019. A novel regulated hybrid promoter that permits autoinduction of heterologous protein expression in *Kluyveromyces lactis*. Appl Environ Microbiol 85:e00542-19. doi.org/10.1128/AEM.00542-19.

Shuman S, 1989, Functional domains of vaccinia virus mRNA capping enzyme. Analysis by limited tryptic digestion. J Biol Chem June 5; 264(16):9690-5.

Wu, S., & Letchworth, G. J. (2004). High efficiency transformation by electroporation of *Pichia pastoris* pretreated with lithium acetate and dithiothreitol. *BioTechniques*, 36(1), 152-154.

What is claimed is:

1. An FCE variant transcript comprising an RNA encoding an amino acid sequence having (a) at least 90% identical to positions 1 to 878 of SEQ ID NO: 1, and (b) a substitution relative to SEQ ID NO: 1 at a position corresponding to positions 215, 337, 572, 648, and 833 of SEQ ID NO: 1, and (c) optionally, a cap.

2. The FCE variant transcript according to claim 1, wherein the substitution is at a position corresponding to positions 215, 337, and 572 of SEQ ID NO: 1.

3. The FCE variant transcript according to claim 1, wherein the encoded amino acid sequence further comprises a second substitution at a position (i) other than the position of the first substitution and (ii) corresponding to position 215, 337, 572, 648, or 833 of SEQ ID NO: 1.

4. The FCE variant transcript according to claim 3, wherein the encoded amino acid sequence further comprises a third substitution at a position (iii) other than the position of the first and second substitutions and (iv) corresponding to position 215, 337, 572, 648, or 833 of SEQ ID NO: 1.

5. The FCE variant transcript according to claim 4, wherein the encoded amino acid sequence further comprises a fourth substitution at a position (v) other than the position of the first, second and third substitutions and (vi) corresponding to position 215, 337, 572, 648, or 833 of SEQ ID NO: 1.

6. A fusion transcript comprising, in a 5' to 3' direction, (I) a nucleotide sequence encoding a purification tag or a sorting signal peptide, and (II) the FCE variant transcript according to claim 1, wherein the purification tag or sorting signal peptide is operably linked to the FCE variant encoded by (II).

7. A fusion transcript comprising, in a 5' to 3' direction, (I) the FCE variant transcript according to claim 1, and (II) a nucleotide sequence encoding a purification tag or a sorting signal peptide, wherein the purification tag or sorting signal peptide is operably linked to the FCE variant encoded by (I).

8. The FCE variant transcript according to claim 1, further comprising (c) a cap.

9. A cell comprising the FCE variant transcript according to claim 2.

10. The cell according to claim 9, wherein the cell is a yeast cell.

11. A method of capping a target RNA, the method comprising contacting (a) an FCE variant having (i) an amino acid sequence at least 90% identical to positions 1 to 878 of SEQ ID NO: 1, and (ii) a substitution at a position corresponding to positions 215, 337, 572, 648, and 833 of SEQ ID NO: 1, (b) the target RNA, and (c) one or more of a cap, an NTP, and a modified NTP, and optionally (d) a buffer, S-adenosylmethionine, and/or an RNase inhibitor, to form a capped target RNA.

12. The method according to claim 11, wherein the contacting further comprises contacting at a temperature in the range of 37° C.-60° C. and/or for a time in the range of seconds to hours.

13. The method according to claim 11, wherein the target RNA is uncapped.

14. The method according to claim 11, further comprising contacting the target RNA with a decapping enzyme prior to contacting the target RNA with the FCE variant.

15. The method according to claim 11, further comprising contacting the capped target RNA with one or more pharmaceutically acceptable additives.

* * * * *

SEQUENCE LISTING

```
<160> NUMBER OF SEQ ID NOS: 28

<210> SEQ ID NO 1
<211> LENGTH: 886
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<223> OTHER INFORMATION: FCE (WT) - 8His polypeptide
```

```
<220> FEATURE:
<221> NAME/KEY: MISC_FEATURE
<222> LOCATION: (215)..(215)
<223> OTHER INFORMATION: asparagine-linked glycosylation site
<220> FEATURE:
<221> NAME/KEY: MISC_FEATURE
<222> LOCATION: (337)..(337)
<223> OTHER INFORMATION: asparagine-linked glycosylation site
<220> FEATURE:
<221> NAME/KEY: MISC_FEATURE
<222> LOCATION: (572)..(572)
<223> OTHER INFORMATION: asparagine-linked glycosylation site
<220> FEATURE:
<221> NAME/KEY: MISC_FEATURE
<222> LOCATION: (648)..(648)
<223> OTHER INFORMATION: asparagine-linked glycosylation site
<220> FEATURE:
<221> NAME/KEY: MISC_FEATURE
<222> LOCATION: (833)..(833)
<223> OTHER INFORMATION: asparagine-linked glycosylation site

<400> SEQUENCE: 1

Ala Lys Arg Leu Gln Arg Cys Gln Asp Val Asn Gln Val Cys Glu Ile
 1               5                  10                  15

Tyr Asn Ser Lys Gly Gly Ile Gly Glu Leu Glu Leu Arg Phe Asp Lys
             20                  25                  30

Leu Pro Gln Asn Leu Phe Ala Gly Val Phe Asp Lys Leu Lys Pro Asp
         35                  40                  45

Gly Glu Ile Gln Thr Thr Met Arg Val Ser Asn Arg Asp Gly Val Ala
     50                  55                  60

Arg Glu Ile Thr Phe Gly Gly Val Lys Thr Asn Glu Ile Phe Val
 65                  70                  75                  80

Lys Lys Gln Asn Ile Cys Val Phe Asp Val Val Asp Ile Phe Ser Tyr
                 85                  90                  95

Lys Val Ala Val Ser Thr Glu Glu Thr Val Val Glu Lys Pro Thr Met
            100                 105                 110

Glu Thr Thr Ala Gly Val Arg Phe Lys Ile Arg Leu Ser Val Glu Asp
        115                 120                 125

Val Val Lys Asp Trp Arg Ile Asp Leu Thr Ala Val Lys Thr Ala Glu
130                 135                 140

Leu Gly Lys Ile Ala Gln His Thr Ala Ser Ile Val Gln Arg Thr Phe
145                 150                 155                 160

Pro Asp Asn Leu Leu Lys Leu Thr Gly Ala Glu Val Ala Lys Leu Ala
                165                 170                 175

Ala Asp Ser Tyr Glu Leu Glu Leu Glu Tyr Thr Gly Lys Ser Pro Ala
            180                 185                 190

Thr Asn Glu Lys Val Asn Val Ala Ala Lys Tyr Ala Val Glu Leu Leu
        195                 200                 205

Ser Ser Val Arg Asn Ala Asn Ser Thr Ala Ala Ser Phe Gly Glu
    210                 215                 220

Ser Val Ser Asp Leu Cys Arg Val Ala Lys Ile Ile His Thr His Glu
225                 230                 235                 240

Tyr Ala Asn Val Val Cys Arg Thr Pro Ser Phe Lys Met Leu Leu Pro
                245                 250                 255

Gln Val Val Ser Leu Thr Lys Ser Ser Tyr Tyr Gly Gly Leu Tyr Pro
            260                 265                 270

Pro Glu Asn Leu Trp Leu Ala Gly Lys Thr Asp Gly Val Arg Ala Leu
        275                 280                 285

Val Val Cys Glu Asp Gly Val Ala Lys Val Ile Thr Ala Glu Ser Val
290                 295                 300
```

-continued

```
Asp Ile Thr His Gly Val Cys Ser Ala Thr Thr Ile Leu Asp Cys Glu
305                 310                 315                 320

Leu Asn Val Asp Ala Lys Ile Leu Tyr Val Phe Asp Val Ile Ile Ser
            325                 330                 335

Asn Asn Thr Gln Val Tyr Thr Gln Pro Phe Ser Thr Arg Ile Thr Thr
                340                 345                 350

Asp Ile Ser Asp Ile Lys Ile Asp Gly Tyr Lys Ile Glu Met Lys Pro
            355                 360                 365

Phe Val Lys Val Val Lys Ala Asp Glu Ala Thr Phe Lys Ser Ala Tyr
        370                 375                 380

Lys Ala Pro His Asn Glu Gly Leu Ile Met Ile Glu Asp Gly Ala Ala
385                 390                 395                 400

Tyr Ala Ala Thr Lys Thr Tyr Lys Trp Lys Pro Leu Ser His Asn Thr
                405                 410                 415

Ile Asp Phe Leu Ile Lys Ala Cys Pro Lys Gln Leu Ile Asn Val Asp
            420                 425                 430

Pro Tyr Lys Pro Arg Ala Gly Tyr Lys Leu Trp Leu Leu Phe Thr Thr
        435                 440                 445

Ile Ser Leu Asp Gln Gln Arg Glu Leu Gly Ile Glu Phe Ile Pro Ala
450                 455                 460

Trp Lys Ile Leu Phe Thr Asp Ile Asn Met Phe Gly Ser Arg Val Pro
465                 470                 475                 480

Ile Gln Phe Gln Pro Ala Ile Asn Pro Leu Ala Tyr Val Cys Tyr Leu
                485                 490                 495

Pro Glu Asp Val Asn Val Asn Asp Gly Asp Ile Val Glu Met Arg Ala
            500                 505                 510

Val Asp Gly Tyr Asp Thr Ile Pro Lys Trp Glu Leu Val Arg Ser Arg
        515                 520                 525

Asn Asp Arg Lys Asn Glu Pro Gly Phe Tyr Gly Asn Asn Tyr Lys Ile
530                 535                 540

Ala Ser Asp Ile Tyr Leu Asn Tyr Ile Asp Val Phe His Phe Glu Asp
545                 550                 555                 560

Leu Tyr Lys Tyr Asn Pro Gly Tyr Phe Glu Lys Asn Lys Ser Asp Ile
                565                 570                 575

Tyr Val Ala Pro Asn Lys Tyr Arg Tyr Leu Ile Lys Ser Leu Phe
            580                 585                 590

Gly Arg Tyr Leu Arg Asp Ala Lys Trp Val Ile Asp Ala Ala Ala Gly
        595                 600                 605

Arg Gly Ala Asp Leu His Leu Tyr Lys Ala Glu Cys Val Glu His Leu
610                 615                 620

Leu Ala Ile Asp Ile Asp Pro Thr Ala Ile Ser Glu Leu Val Arg Arg
625                 630                 635                 640

Arg Asn Glu Ile Thr Gly Tyr Asn Lys Ser His Arg Gly Gly Arg Asn
                645                 650                 655

Met His Ser His Arg Gly Gln Ser His Cys Ala Lys Ser Thr Ser Leu
            660                 665                 670

His Ala Leu Val Ala Asp Leu Arg Glu Asn Pro Asp Val Leu Ile Pro
        675                 680                 685

Lys Ile Ile Gln Ser Arg Pro His Glu Arg Cys Tyr Asp Ala Ile Val
690                 695                 700
```

```
Ile Asn Phe Ala Ile His Tyr Leu Cys Asp Thr Asp Glu His Ile Arg
705                 710                 715                 720

Asp Phe Leu Ile Thr Val Ser Arg Leu Leu Ala Pro Asn Gly Val Phe
            725                 730                 735

Ile Phe Thr Thr Met Asp Gly Glu Ser Ile Val Lys Leu Leu Ala Asp
                740                 745                 750

His Lys Val Arg Pro Gly Glu Ala Trp Thr Ile His Thr Gly Asp Val
            755                 760                 765

Asn Ser Pro Asp Ser Thr Val Pro Lys Tyr Ser Ile Arg Arg Leu Tyr
        770                 775                 780

Asp Ser Asp Lys Leu Thr Lys Thr Gly Gln Gln Ile Glu Val Leu Leu
785                 790                 795                 800

Pro Met Ser Gly Glu Met Lys Ala Glu Pro Leu Cys Asn Ile Lys Asn
                805                 810                 815

Ile Ile Ser Met Ala Arg Lys Met Gly Leu Asp Leu Val Glu Ser Ala
                820                 825                 830

Asn Phe Ser Val Leu Tyr Glu Ala Tyr Ala Arg Asp Tyr Pro Asp Ile
        835                 840                 845

Tyr Ala Arg Met Thr Pro Asp Asp Lys Leu Tyr Asn Asp Leu His Thr
850                 855                 860

Tyr Ala Val Phe Lys Arg Lys Lys Gly Ala Ser Ala Thr Ser His His
865                 870                 875                 880

His His His His His His
                885

<210> SEQ ID NO 2
<211> LENGTH: 1274
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<223> OTHER INFORMATION: MBP-FCE-8His polypeptide
<220> FEATURE:
<221> NAME/KEY: MISC_FEATURE
<222> LOCATION: (1)..(388)
<223> OTHER INFORMATION: maltose binding protein (MBP) (367 aa) +
      Linker + Enterokinase (EK) cleavage sequence (DDDK)
<220> FEATURE:
<221> NAME/KEY: MISC_FEATURE
<222> LOCATION: (389)..(1274)
<223> OTHER INFORMATION: FCE mRNA Capping enzyme (878 aa) + 8xHis-tag
<220> FEATURE:
<221> NAME/KEY: MISC_FEATURE
<222> LOCATION: (603)..(603)
<223> OTHER INFORMATION: asparagine-linked glycosylation site
<220> FEATURE:
<221> NAME/KEY: MISC_FEATURE
<222> LOCATION: (725)..(725)
<223> OTHER INFORMATION: asparagine-linked glycosylation site
<220> FEATURE:
<221> NAME/KEY: MISC_FEATURE
<222> LOCATION: (960)..(960)
<223> OTHER INFORMATION: asparagine-linked glycosylation site
<220> FEATURE:
<221> NAME/KEY: MISC_FEATURE
<222> LOCATION: (1036)..(1036)
<223> OTHER INFORMATION: asparagine-linked glycosylation site
<220> FEATURE:
<221> NAME/KEY: MISC_FEATURE
<222> LOCATION: (1221)..(1221)
<223> OTHER INFORMATION: asparagine-linked glycosylation site
```

<400> SEQUENCE: 2

```
Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Glu Leu Val Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
        355                 360                 365

Ser Ser Ser Asn Asn Asn Asn Asn Asn Asn Asn Asn Asn Leu Gly Asp
    370                 375                 380

Asp Asp Asp Lys Ala Lys Arg Leu Gln Arg Cys Gln Asp Val Asn Gln
385                 390                 395                 400

Val Cys Glu Ile Tyr Asn Ser Lys Gly Gly Ile Gly Glu Leu Glu Leu
                405                 410                 415
```

```
Arg Phe Asp Lys Leu Pro Gln Asn Leu Phe Ala Gly Val Phe Asp Lys
            420                 425                 430

Leu Lys Pro Asp Gly Glu Ile Gln Thr Thr Met Arg Val Ser Asn Arg
        435                 440                 445

Asp Gly Val Ala Arg Glu Ile Thr Phe Gly Gly Val Lys Thr Asn
    450                 455                 460

Glu Ile Phe Val Lys Lys Gln Asn Ile Cys Val Phe Asp Val Val Asp
465                 470                 475                 480

Ile Phe Ser Tyr Lys Val Ala Val Ser Thr Glu Glu Thr Val Val Glu
                485                 490                 495

Lys Pro Thr Met Glu Thr Thr Ala Gly Val Arg Phe Lys Ile Arg Leu
            500                 505                 510

Ser Val Glu Asp Val Val Lys Asp Trp Arg Ile Asp Leu Thr Ala Val
        515                 520                 525

Lys Thr Ala Glu Leu Gly Lys Ile Ala Gln His Thr Ala Ser Ile Val
    530                 535                 540

Gln Arg Thr Phe Pro Asp Asn Leu Leu Lys Leu Thr Gly Ala Glu Val
545                 550                 555                 560

Ala Lys Leu Ala Ala Asp Ser Tyr Glu Leu Glu Leu Glu Tyr Thr Gly
                565                 570                 575

Lys Ser Pro Ala Thr Asn Glu Lys Val Asn Val Ala Ala Lys Tyr Ala
            580                 585                 590

Val Glu Leu Leu Ser Ser Val Arg Asn Ala Asn Ser Thr Ala Ala Ala
        595                 600                 605

Ser Phe Gly Glu Ser Val Ser Asp Leu Cys Arg Val Ala Lys Ile Ile
    610                 615                 620

His Thr His Glu Tyr Ala Asn Val Val Cys Arg Thr Pro Ser Phe Lys
625                 630                 635                 640

Met Leu Leu Pro Gln Val Val Ser Leu Thr Lys Ser Ser Tyr Tyr Gly
                645                 650                 655

Gly Leu Tyr Pro Pro Glu Asn Leu Trp Leu Ala Gly Lys Thr Asp Gly
            660                 665                 670

Val Arg Ala Leu Val Val Cys Glu Asp Gly Val Ala Lys Val Ile Thr
        675                 680                 685

Ala Glu Ser Val Asp Ile Thr His Gly Val Cys Ser Ala Thr Thr Ile
    690                 695                 700

Leu Asp Cys Glu Leu Asn Val Asp Ala Lys Ile Leu Tyr Val Phe Asp
705                 710                 715                 720

Val Ile Ile Ser Asn Asn Thr Gln Val Tyr Thr Gln Pro Phe Ser Thr
                725                 730                 735

Arg Ile Thr Thr Asp Ile Ser Asp Ile Lys Ile Asp Gly Tyr Lys Ile
            740                 745                 750

Glu Met Lys Pro Phe Val Lys Val Lys Ala Asp Glu Ala Thr Phe
        755                 760                 765

Lys Ser Ala Tyr Lys Ala Pro His Asn Glu Gly Leu Ile Met Ile Glu
    770                 775                 780

Asp Gly Ala Ala Tyr Ala Ala Thr Lys Thr Tyr Lys Trp Lys Pro Leu
785                 790                 795                 800

Ser His Asn Thr Ile Asp Phe Leu Ile Lys Ala Cys Pro Lys Gln Leu
                805                 810                 815

Ile Asn Val Asp Pro Tyr Lys Pro Arg Ala Gly Tyr Lys Leu Trp Leu
            820                 825                 830
```

```
Leu Phe Thr Thr Ile Ser Leu Asp Gln Gln Arg Glu Leu Gly Ile Glu
835                 840                 845

Phe Ile Pro Ala Trp Lys Ile Leu Phe Thr Asp Ile Asn Met Phe Gly
850                 855                 860

Ser Arg Val Pro Ile Gln Phe Gln Pro Ala Ile Asn Pro Leu Ala Tyr
865                 870                 875                 880

Val Cys Tyr Leu Pro Glu Asp Val Asn Val Asn Asp Gly Asp Ile Val
                885                 890                 895

Glu Met Arg Ala Val Asp Gly Tyr Asp Thr Ile Pro Lys Trp Glu Leu
            900                 905                 910

Val Arg Ser Arg Asn Asp Arg Lys Asn Glu Pro Gly Phe Tyr Gly Asn
        915                 920                 925

Asn Tyr Lys Ile Ala Ser Asp Ile Tyr Leu Asn Tyr Ile Asp Val Phe
    930                 935                 940

His Phe Glu Asp Leu Tyr Lys Tyr Asn Pro Gly Tyr Phe Glu Lys Asn
945                 950                 955                 960

Lys Ser Asp Ile Tyr Val Ala Pro Asn Lys Tyr Arg Arg Tyr Leu Ile
                965                 970                 975

Lys Ser Leu Phe Gly Arg Tyr Leu Arg Asp Ala Lys Trp Val Ile Asp
            980                 985                 990

Ala Ala Ala Gly Arg Gly Ala Asp Leu His Leu Tyr Lys Ala Glu Cys
        995                 1000                1005

Val Glu His Leu Leu Ala Ile Asp Ile Asp Pro Thr Ala Ile Ser
    1010                1015                1020

Glu Leu Val Arg Arg Arg Asn Glu Ile Thr Gly Tyr Asn Lys Ser
    1025                1030                1035

His Arg Gly Gly Arg Asn Met His Ser His Arg Gly Gln Ser His
    1040                1045                1050

Cys Ala Lys Ser Thr Ser Leu His Ala Leu Val Ala Asp Leu Arg
    1055                1060                1065

Glu Asn Pro Asp Val Leu Ile Pro Lys Ile Ile Gln Ser Arg Pro
    1070                1075                1080

His Glu Arg Cys Tyr Asp Ala Ile Val Ile Asn Phe Ala Ile His
    1085                1090                1095

Tyr Leu Cys Asp Thr Asp Glu His Ile Arg Asp Phe Leu Ile Thr
    1100                1105                1110

Val Ser Arg Leu Leu Ala Pro Asn Gly Val Phe Ile Phe Thr Thr
    1115                1120                1125

Met Asp Gly Glu Ser Ile Val Lys Leu Leu Ala Asp His Lys Val
    1130                1135                1140

Arg Pro Gly Glu Ala Trp Thr Ile His Thr Gly Asp Val Asn Ser
    1145                1150                1155

Pro Asp Ser Thr Val Pro Lys Tyr Ser Ile Arg Arg Leu Tyr Asp
    1160                1165                1170

Ser Asp Lys Leu Thr Lys Thr Gly Gln Gln Ile Glu Val Leu Leu
    1175                1180                1185

Pro Met Ser Gly Glu Met Lys Ala Glu Pro Leu Cys Asn Ile Lys
    1190                1195                1200

Asn Ile Ile Ser Met Ala Arg Lys Met Gly Leu Asp Leu Val Glu
    1205                1210                1215

Ser Ala Asn Phe Ser Val Leu Tyr Glu Ala Tyr Ala Arg Asp Tyr
    1220                1225                1230
```

```
Pro Asp Ile Tyr Ala Arg Met Thr Pro Asp Asp Lys Leu Tyr Asn
    1235            1240                1245

Asp Leu His Thr Tyr Ala Val Phe Lys Arg Lys Lys Gly Ala Ser
    1250            1255                1260

Ala Thr Ser His His His  His His His His
    1265            1270

<210> SEQ ID NO 3
<211> LENGTH: 38
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Forward primer for amplification of an FCE
      variant

<400> SEQUENCE: 3
agaaaagaga ggccgaagct gcgaagcgtc tgcagcgt                           38

<210> SEQ ID NO 4
<211> LENGTH: 38
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Reverse primer for amplification of an FCE
      variant

<400> SEQUENCE: 4
agaaaagaga ggccgaagct gcgaagcgtc tgcagcgt                           38

<210> SEQ ID NO 5
<211> LENGTH: 18
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Forward primer for amplification of the FCE
      vector fragment

<400> SEQUENCE: 5
aggggcggcc gctcaaga                                                 18

<210> SEQ ID NO 6
<211> LENGTH: 19
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Reverse primer for amplification of the FCE
      vector fragment

<400> SEQUENCE: 6
agcttcggcc tctcttttc                                                19

<210> SEQ ID NO 7
<211> LENGTH: 23
<212> TYPE: DNA
<213> ORGANISM: Artificial Sequence
```

```
<220> FEATURE:
<223> OTHER INFORMATION: Synthetic construct
<220> FEATURE:
<221> NAME/KEY: misc_feature
<223> OTHER INFORMATION: Forward primer N215Q- Fwd

<400> SEQUENCE: 7
tcgtaacgcg caaagcaccg cgg                                          23

<210> SEQ ID NO 8
<211> LENGTH: 20
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Reverse primer N215Q-Rev

<400> SEQUENCE: 8
acgctgctca gcagctccac                                              20

<210> SEQ ID NO 9
<211> LENGTH: 30
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Forward primer N337Q-Fwd

<400> SEQUENCE: 9
tatcattagc caaaacaccc aggtttatac                                   30

<210> SEQ ID NO 10
<211> LENGTH: 18
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Reverse primer N337Q-Rev

<400> SEQUENCE: 10
acgtcgaaca cgtacaga                                                18

<210> SEQ ID NO 11
<211> LENGTH: 29
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Forward primer N572Q-Fwd

<400> SEQUENCE: 11
cttcgagaag caaaaaagcg atatctatg                                    29

<210> SEQ ID NO 12
<211> LENGTH: 18
<212> TYPE: DNA
<213> ORGANISM: Artificial Sequence
<220> FEATURE:
<223> OTHER INFORMATION: Synthetic construct
```

```
<220> FEATURE:
<221> NAME/KEY: misc_feature
<223> OTHER INFORMATION: Reverse primer N572Q-Rev

<400> SEQUENCE: 12
tagcccgggt tatacttg                                                    18

<210> SEQ ID NO 13
<211> LENGTH: 30
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Forward primer N648Q-Fwd

<400> SEQUENCE: 13
accggctacc aaaagagcca ccgtggcggt                                       30

<210> SEQ ID NO 14
<211> LENGTH: 30
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Reverse primer N648Q-Rev

<400> SEQUENCE: 14
gtggctcttt tggtagccgg taatctcgtt                                       30

<210> SEQ ID NO 15
<211> LENGTH: 30
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Forward primer N833Q-Fwd

<400> SEQUENCE: 15
gaaagcgcgc aattcagcgt gctgtacgag                                       30

<210> SEQ ID NO 16
<211> LENGTH: 30
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Reverse primer N833Q-Rev

<400> SEQUENCE: 16
cacgctgaat tgcgcgcttt caaccagatc                                       30

<210> SEQ ID NO 17
<211> LENGTH: 38
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Forward primer for amplification of an FCE
      variant
```

<400> SEQUENCE: 17
tcggggatga cgatgacaag gcgaagcgtc tgcagcgt                                38

<210> SEQ ID NO 18
<211> LENGTH: 39
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Reverse primer for amplification of an FCE
      variant

<400> SEQUENCE: 18
tcagcctctc ttttctcgag ttagtggtgg tggtggtgg                               39

<210> SEQ ID NO 19
<211> LENGTH: 24
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Forward primer for amplification of a pKLMF-EK
      vector fragment

<400> SEQUENCE: 19
ctcgagaaaa gagaggctga agct                                               24

<210> SEQ ID NO 20
<211> LENGTH: 21
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Reverse primer for amplification of a pKLMF-EK
      vector fragment

<400> SEQUENCE: 20
cttgtcatcg tcatccccga g                                                  21

<210> SEQ ID NO 21
<211> LENGTH: 23
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Forward primer for amplification of the FCE
      assembled linear expression cassette

<400> SEQUENCE: 21
gatcgactca taaaatagta acc                                                23

<210> SEQ ID NO 22
<211> LENGTH: 25
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Reverse primer for amplification of the FCE
      assembled linear expression cassette

```
<400> SEQUENCE: 22
ccgcggaaat ttaggaattt taaac                                           25

<210> SEQ ID NO 23
<211> LENGTH: 25
<212> TYPE: RNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Substrate RNA for in vitro capping reaction

<400> SEQUENCE: 23
guagaacuuc gucgaguacg cucaa                                           25

<210> SEQ ID NO 24
<211> LENGTH: 6494
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: PD912 vector
<220> FEATURE:
<221> NAME/KEY: misc_feature
<222> LOCATION: (1157)..(1639)
<223> OTHER INFORMATION: Pichia GAP promoter
<220> FEATURE:
<221> NAME/KEY: misc_feature
<222> LOCATION: (1650)..(1916)
<223> OTHER INFORMATION: DNA encoding alpha mating factor signal peptide
<220> FEATURE:
<221> NAME/KEY: misc_feature
<222> LOCATION: (1917)..(4577)
<223> OTHER INFORMATION: DNA encoding FCE mRNA Capping enzyme (878 aa) +
      8xHis-tag
<220> FEATURE:
<221> NAME/KEY: misc_feature
<222> LOCATION: (2559)..(2561)
<223> OTHER INFORMATION: asparagine to glutamine variant codon
<220> FEATURE:
<221> NAME/KEY: misc_feature
<222> LOCATION: (2925)..(2927)
<223> OTHER INFORMATION: asparagine to glutamine variant codon
<220> FEATURE:
<221> NAME/KEY: misc_feature
<222> LOCATION: (3630)..(3632)
<223> OTHER INFORMATION: asparagine to glutamine variant codon

<400> SEQUENCE: 24
gcttcagcag agcgcagata ccaaatactg ttcttctagt gtagccgtag ttaggccacc     60
acttcaagaa ctctgtagca ccgcctacat acctcgctct gctaatcctg ttaccagtgg    120
ctgctgccag tggcgataag tcgtgtctta ccgggttgga ctcaagacga tagttaccgg    180
ataaggcgca gcggtcgggc tgaacggggg gttcgtgcac acagcccagc ttggagcgaa    240
cgacctacac cgaactgaga tacctacagc gtgagctatg agaaagcgcc acgcttcccg    300
aagggagaaa ggcggacagg tatccggtaa gcggcagggt cggaacagga gagcgcacga    360
gggagcttcc aggggaaac gcctggtatc tttatagtcc tgtcgggttt cgccacctct    420
gacttgagcg tcgatttttg tgatgctcgt caggggggcg gagcctatgg aaaaacgcca    480
gcaacgcggc cttttacgg ttcctggcct tttgctggcc ttttgctcac atgttctttc    540
ctgcggtacc cagatccaat tcccgctttg actgctgaa atctccatcg cctacaatga    600
tgacatttgg atttggttga ctcatgttgg tattgtgaaa tagacgcaga tcgggaacac    660
```

```
tgaaaaatac acagttatta ttcatttaaa taacatccaa agacgaaagg ttgaatgaaa    720
ccttttttgcc atccgacatc cacaggtcca ttctcacaca taagtgccaa acgcaacagg    780
agggataca  ctagcagcag accgttgcaa acgcaggacc tccactcctc ttctcctcaa    840
cacccacttt tgccatcgaa aaaccagccc agttattggg cttgattgga gctcgctcat    900
tccaattcct tctattaggc tactaacacc atgactttat tagcctgtct atcctggccc    960
ccctggcgag gttcatgttt gtttatttcc gaatgcaaca agctccgcat tacacccgaa   1020
catcactcca gatgagggct ttctgagtgt ggggtcaaat agtttcatgt tccccaaatg   1080
gcccaaaact gacagtttaa acgctgtctt ggaacctaat atgacaaaag cgtgatctca   1140
tccaagatga actaaggatc cttttttgta gaaatgtctt ggtgtcctcg tccaatcagg   1200
tagccatctc tgaaatatct ggctccgttg caactccgaa cgacctgctg gcaacgtaaa   1260
attctccggg gtaaaactta aatgtggagt aatggaacca gaaacgtctc ttcccttctc   1320
tctccttcca ccgcccgtta ccgtccctag gaaattttac tctgctggag agcttcttct   1380
acggcccct  tgcagcaatg ctcttcccag cattacgttg cgggtaaaac ggaggtcgtg   1440
tacccgacct agcagcccag ggatggaaaa gtcccggccg tcgctggcaa taatagcggg   1500
cggacgcatg tcatgagatt attggaaacc accagaatcg aatataaaag gcgaacacct   1560
ttcccaattt tggtttctcc tgacccaaag actttaaatt taatttattt gtccctattt   1620
caatcaattg aacaactatt tccgaaacga tgagattccc atctattttc accgctgtct   1680
tgttcgctgc ctcctctgca ttggctgccc ctgttaacac taccactgaa gacgagactg   1740
ctcaaattcc agctgaagca gttatcggtt actctgacct tgagggtgat ttcgacgtcg   1800
ctgttttgcc tttctctaac tccactaaca acggtttgtt gttcattaac accactatcg   1860
cttccattgc tgctaaggaa gagggtgtct ctctcgagaa aagagaggcc gaagctgcga   1920
agcgtctgca gcgttgccaa gatgtgaacc aggtttgcga aatctacaac agcaagggtg   1980
gcattggcga gctggaactg cgtttcgaca aactgccgca gaacctgttc gcgggcgtgt   2040
ttgataagct gaaaccggac ggcgagatcc aaaccaccat gcgtgtgagc aaccgtgacg   2100
gtgttgcgcg tgaaattacc ttcggtggcg gtgtgaaaac caacgagatc ttcgttaaga   2160
aacaaaacat ttgcgtgttc gacgtggttg atatctttag ctacaaggtg gcggttagca   2220
ccgaggaaac cgtggttgaa aaaccgacca tggagaccac cgcgggcgtt cgtttcaaaa   2280
tccgtctgag cgtggaagac gtggttaagg attggcgtat tgacctgacc gcggttaaga   2340
ccgcggagct gggtaaaatc gcgcagcaca ccgcgcagat tgtgcaacgt acctttccgg   2400
ataacctgct gaagctgacc ggtgcggaag tggcgaaact ggcggcggac agctacgagc   2460
tggaactgga gtataccggc aagagcccgg cgaccaacga aaaggtgaac gttgcggcga   2520
aatacgcggt ggagctgctg agcagcgttc gtaacgcgca aagcaccgcg gcggcgagct   2580
ttggtgaaag cgtgagcgac ctgtgccgtg ttgcgaaaat cattcacacc cacgagtacg   2640
cgaacgtggt ttgccgtacc ccgagcttta aaatgctgct gccgcaggtg gttagcctga   2700
ccaagagcag ctactatggc ggtctgtatc cgccggaaaa cctgtggctg cgggcaaga   2760
ccgatggtgt tcgtgcgctg gttgtgtgcg aagacgcgt  ggcgaaagtt atcaccgcgg   2820
agagcgtgga tattacccac ggtgtttgca gcgcgaccac catcctggat tgcgagctga   2880
acgtggacgc gaaagattctg tacgtgttcg acgttatcat tagccaaaac acccaggttt   2940
atacccaacc gttagcacc  cgtatcacca ccgacattag cgatatcaag atcgatggtt   3000
acaagatcga aatgaagccg ttcgtgaagg tggttaaagc ggacgaggcg accttttaaga   3060
```

```
gcgcgtataa agcgccgcac aacgaaggcc tgatcatgat tgaggatggt gcggcgtacg   3120
cggcgaccaa gacctataag tggaaaccgc tgagccacaa caccatcgat ttcctgatta   3180
aggcgtgccc gaaacagctg atcaacgttg acccgtacaa gccgcgtgcg ggttataaac   3240
tgtggctgct gttcaccacc attagcctgg atcagcaacg tgaactgggc atcgagttta   3300
ttccggcgtg gaaaatcctg ttcaccgaca ttaacatgtt tggtagccgt gttccgatcc   3360
agttccaacc ggcgattaac ccgctggcgt acgtgtgcta tctgccggaa gacgtgaacg   3420
ttaacgacgg cgatatcgtg gagatgcgtg cggttgacgg ttacgatacc attccgaaat   3480
gggaactggt gcgtagccgt aacgatcgta agaacgagcc gggcttttac ggtaacaact   3540
ataaaatcgc gagcgacatt tacctgaact atatcgatgt gttccacttt gaagacctgt   3600
acaagtataa cccgggctac ttcgagaagc aaaaaagcga tatctatgtt gcgccgaaca   3660
agtaccgtcg ttatctgatt aaaagcctgt ttggtcgtta cctgcgtgat gcgaaatggg   3720
ttattgatgc ggcggcgggt cgtggtgcgg acctgcacct gtataaagcg gaatgcgtgg   3780
agcacctgct ggcgatcgac attgatccga ccgcgatcag cgaactggtt cgtcgtcgta   3840
acgagattac cggctacaac aagagccacc gtggcggtcg taacatgcac agccaccgtg   3900
gtcagagcca ctgcgcgaaa agcaccagcc tgcacgcgct ggttgcggat ctgcgtgaaa   3960
acccggacgt gctgatcccg aagatcattc aaagccgtcc gcacgagcgt tgctacgatg   4020
cgatcgtgat taacttcgcg attcactatc tgtgcgacac cgatgaacac atccgtgact   4080
ttctgattac cgttagccgt ctgctggcgc cgaacggtgt gttcatcttt accaccatgg   4140
atggtgaaag cattgttaag ctgctggcgg accacaaagt tcgtccgggt gaagcgtgga   4200
ccatccacac cggtgatgtt aacagcccgg acagcaccgt gccgaaatac agcatccgtc   4260
gtctgtatga cagcgataag ctgaccaaaa ccggccagca aattgaggtg ctgctgccga   4320
tgagcggtga aatgaaggcg gagccgctgt gcaacatcaa aaacatcatt agcatggcgc   4380
gtaagatggg cctggatctg gttgaaagcg cgaacttcag cgtgctgtac gaggcgtatg   4440
cgcgtgacta cccggatatc tatgcgcgta tgaccccgga cgataagctg tacaacgacc   4500
tgcacaccta tgcggttttt aagcgtaaga aaggtgcgag cgcgaccagc catcatcacc   4560
accaccacca ccactaaagg ttgaaggggc ggccgctcaa gaggatgtca gaatgccatt   4620
tgcctgagag atgcaggctt cattttttgat actttttat ttgtaaccta tatagtatag   4680 gattttttt gtcattttgt ttcttctcgt acgagcttgc tcctgatcag cctatctcgc   4740
agcagatgaa tatcttgtgg tagggggtttg ggaaaatcat tcgagtttga tgttttcttt   4800
ggtatttccc actcctcttc agagtacaga agattaagtg aaaccttcgt ttgtgcggat   4860
ccttcagtaa tgtcttgttt cttttgttgc agtggtgagc cattttgact tcgtgaaagt   4920
ttctttagaa tagttgtttc cagaggccaa acattccacc cgtagtaaag tgcaagcgta   4980
ggaagaccaa gactggcata aatcaggtat aagtgtcgag cactggcagg tgatcttctg   5040
aaagtttcta ctagcagata agatccagta gtcatgcata tggcaacaat gtaccgtgtg   5100
gatctaagaa cgcgtcctac taaccttcgc attcgttggt ccagtttgtt gttatcgatc   5160
aacgtgacaa ggttgtcgat tccgcgtaag catgcatacc caaggacgcc tgttgcaatt   5220
ccaagtgagc cagttccaac aatctttgta atattagagc acttcattgt gttgcgcttg   5280
aaagtaaaat gcgaacaaat taagagataa tctcgaaacc gcgacttcaa acgccaatat   5340
gatgtgcggc acacaataag cgttcatatc cgctgggtga cttctcgct ttaaaaaatt   5400 atccgaaaaa attttctaga gtgttgttac tttatacttc cggctcgtat aatacgacaa   5460
```

```
ggtgtaagga ggactaaacc atggctaaac tcacctctgc tgttccagtc ctgactgctc   5520
gtgatgttgc tggtgctgtt gagttctgga ctgatagact cggtttctcc cgtgacttcg   5580
tagaggacga ctttgccggt gttgtacgtg acgacgttac cctgttcatc tccgcagttc   5640
aggaccaggt tgtgccagac aacactctgg catgggtatg ggttcgtggt ctggacgaac   5700
tgtacgctga gtggtctgag gtcgtgtcta ccaacttccg tgatgcatct ggtccagcta   5760
tgaccgagat cggtgaacag ccctggggtc gtgagtttgc actgcgtgat ccagctggta   5820
actgcgtgca tttcgtcgca gaagaacagg actaacaatt gacaccttac gattatttag   5880
agagtattta ttagttttat tgtatgtata cggatgtttt attatctatt tatgccctta   5940
tattctgtaa ctatccaaaa gtcctatctt atcaagccag caatctatgt ccgcgaacgt   6000
caactaaaaa taagcttttt atgctgttct ctcttttttt cccttcggta taattatacc   6060
ttgcatccac agattctcct gccaaatttt gcataatcct ttacaacatg gctatatggg   6120
agcacttagc gccctccaaa acccatattg cctacgcatg tataggtgtt ttttccacaa   6180
tattttctct gtgctctctt tttattaaag agaagctcta tatcggagaa gcttctgtgg   6240
ccgttatatt cggccttatc gtgggaccac attgcctgaa ttggtttgcc ccggaagatt   6300
ggggaaactt ggatctgatt accttagctg caggtaccac tgagcgtcag accccgtaga   6360
aaagatcaaa ggatcttctt gagatccttt ttttctgcgc gtaatctgct gcttgcaaac   6420
aaaaaaacca ccgctaccag cggtggtttg tttgccggat caagagctac caactctttt   6480
tccgaaggta actg                                                     6494
```

```

<210> SEQ ID NO 25
<211> LENGTH: 886
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<223> OTHER INFORMATION: Fully processed mature FCE variant protein

<400> SEQUENCE: 25

Ala Lys Arg Leu Gln Arg Cys Gln Asp Val Asn Gln Val Cys Glu Ile
1               5                   10                  15

Tyr Asn Ser Lys Gly Gly Ile Gly Glu Leu Glu Leu Arg Phe Asp Lys
            20                  25                  30

Leu Pro Gln Asn Leu Phe Ala Gly Val Phe Asp Lys Leu Lys Pro Asp
        35                  40                  45

Gly Glu Ile Gln Thr Thr Met Arg Val Ser Asn Arg Asp Gly Val Ala
    50                  55                  60

Arg Glu Ile Thr Phe Gly Gly Gly Val Lys Thr Asn Glu Ile Phe Val
65                  70                  75                  80

Lys Lys Gln Asn Ile Cys Val Phe Asp Val Val Asp Ile Phe Ser Tyr
                85                  90                  95

Lys Val Ala Val Ser Thr Glu Glu Thr Val Val Glu Lys Pro Thr Met
            100                 105                 110

Glu Thr Thr Ala Gly Val Arg Phe Lys Ile Arg Leu Ser Val Glu Asp
        115                 120                 125

Val Val Lys Asp Trp Arg Ile Asp Leu Thr Ala Val Lys Thr Ala Glu
    130                 135                 140

Leu Gly Lys Ile Ala Gln His Thr Ala Ser Ile Val Gln Arg Thr Phe
145                 150                 155                 160
```

```
Pro Asp Asn Leu Leu Lys Leu Thr Gly Ala Glu Val Ala Lys Leu Ala
            165                 170                 175
Ala Asp Ser Tyr Glu Leu Glu Leu Glu Tyr Thr Gly Lys Ser Pro Ala
        180                 185                 190
Thr Asn Glu Lys Val Asn Val Ala Ala Lys Tyr Ala Val Glu Leu Leu
    195                 200                 205
Ser Ser Val Arg Asn Ala Gln Ser Thr Ala Ala Ser Phe Gly Glu
210                 215                 220
Ser Val Ser Asp Leu Cys Arg Val Ala Lys Ile Ile His Thr His Glu
225                 230                 235                 240
Tyr Ala Asn Val Val Cys Arg Thr Pro Ser Phe Lys Met Leu Leu Pro
                245                 250                 255
Gln Val Val Ser Leu Thr Lys Ser Ser Tyr Tyr Gly Gly Leu Tyr Pro
            260                 265                 270
Pro Glu Asn Leu Trp Leu Ala Gly Lys Thr Asp Gly Val Arg Ala Leu
        275                 280                 285
Val Val Cys Glu Asp Gly Val Ala Lys Val Ile Thr Ala Glu Ser Val
    290                 295                 300
Asp Ile Thr His Gly Val Cys Ser Ala Thr Thr Ile Leu Asp Cys Glu
305                 310                 315                 320
Leu Asn Val Asp Ala Lys Ile Leu Tyr Val Phe Asp Val Ile Ile Ser
                325                 330                 335
Gln Asn Thr Gln Val Tyr Thr Gln Pro Phe Ser Thr Arg Ile Thr Thr
            340                 345                 350
Asp Ile Ser Asp Ile Lys Ile Asp Gly Tyr Lys Ile Glu Met Lys Pro
        355                 360                 365
Phe Val Lys Val Val Lys Ala Asp Glu Ala Thr Phe Lys Ser Ala Tyr
    370                 375                 380
Lys Ala Pro His Asn Glu Gly Leu Ile Met Ile Glu Asp Gly Ala Ala
385                 390                 395                 400
Tyr Ala Ala Thr Lys Thr Tyr Lys Trp Lys Pro Leu Ser His Asn Thr
                405                 410                 415
Ile Asp Phe Leu Ile Lys Ala Cys Pro Lys Gln Leu Ile Asn Val Asp
            420                 425                 430
Pro Tyr Lys Pro Arg Ala Gly Tyr Lys Leu Trp Leu Leu Phe Thr Thr
        435                 440                 445
Ile Ser Leu Asp Gln Gln Arg Glu Leu Gly Ile Glu Phe Ile Pro Ala
    450                 455                 460
Trp Lys Ile Leu Phe Thr Asp Ile Asn Met Phe Gly Ser Arg Val Pro
465                 470                 475                 480
Ile Gln Phe Gln Pro Ala Ile Asn Pro Leu Ala Tyr Val Cys Tyr Leu
                485                 490                 495
Pro Glu Asp Val Asn Val Asn Asp Gly Asp Ile Val Glu Met Arg Ala
            500                 505                 510
Val Asp Gly Tyr Asp Thr Ile Pro Lys Trp Glu Leu Val Arg Ser Arg
        515                 520                 525
Asn Asp Arg Lys Asn Glu Pro Gly Phe Tyr Gly Asn Asn Tyr Lys Ile
    530                 535                 540
Ala Ser Asp Ile Tyr Leu Asn Tyr Ile Asp Val Phe His Phe Glu Asp
545                 550                 555                 560
Leu Tyr Lys Tyr Asn Pro Gly Tyr Phe Glu Lys Gln Lys Ser Asp Ile
                565                 570                 575
```

Tyr Val Ala Pro Asn Lys Tyr Arg Arg Tyr Leu Ile Lys Ser Leu Phe
            580                 585                 590

Gly Arg Tyr Leu Arg Asp Ala Lys Trp Val Ile Asp Ala Ala Ala Gly
        595                 600                 605

Arg Gly Ala Asp Leu His Leu Tyr Lys Ala Glu Cys Val Glu His Leu
    610                 615                 620

Leu Ala Ile Asp Ile Asp Pro Thr Ala Ile Ser Glu Leu Val Arg Arg
625                 630                 635                 640

Arg Asn Glu Ile Thr Gly Tyr Asn Lys Ser His Arg Gly Gly Arg Asn
                645                 650                 655

Met His Ser His Arg Gly Gln Ser His Cys Ala Lys Ser Thr Ser Leu
            660                 665                 670

His Ala Leu Val Ala Asp Leu Arg Glu Asn Pro Asp Val Leu Ile Pro
        675                 680                 685

Lys Ile Ile Gln Ser Arg Pro His Glu Arg Cys Tyr Asp Ala Ile Val
    690                 695                 700

Ile Asn Phe Ala Ile His Tyr Leu Cys Asp Thr Asp Glu His Ile Arg
705                 710                 715                 720

Asp Phe Leu Ile Thr Val Ser Arg Leu Leu Ala Pro Asn Gly Val Phe
                725                 730                 735

Ile Phe Thr Thr Met Asp Gly Glu Ser Ile Val Lys Leu Leu Ala Asp
            740                 745                 750

His Lys Val Arg Pro Gly Glu Ala Trp Thr Ile His Thr Gly Asp Val
        755                 760                 765

Asn Ser Pro Asp Ser Thr Val Pro Lys Tyr Ser Ile Arg Arg Leu Tyr
770                 775                 780

Asp Ser Asp Lys Leu Thr Lys Thr Gly Gln Gln Ile Glu Val Leu Leu
                785                 790                 795                 800

Pro Met Ser Gly Glu Met Lys Ala Glu Pro Leu Cys Asn Ile Lys Asn
            805                 810                 815

Ile Ile Ser Met Ala Arg Lys Met Gly Leu Asp Leu Val Glu Ser Ala
        820                 825                 830

Asn Phe Ser Val Leu Tyr Glu Ala Tyr Ala Arg Asp Tyr Pro Asp Ile
    835                 840                 845

Tyr Ala Arg Met Thr Pro Asp Asp Lys Leu Tyr Asn Asp Leu His Thr
850                 855                 860

Tyr Ala Val Phe Lys Arg Lys Gly Ala Ser Ala Thr Ser His His
865                 870                 875                 880

His His His His His His
            885

<210> SEQ ID NO 26
<211> LENGTH: 6494
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: pD912 vector
<220> FEATURE:
<221> NAME/KEY: misc_feature
<222> LOCATION: (1157)..(1639)
<223> OTHER INFORMATION: Pichia GAP promoter
<220> FEATURE:
<221> NAME/KEY: misc_feature
<222> LOCATION: (1650)..(1916)
<223> OTHER INFORMATION: DNA encoding alpha mating factor signal peptide

```
<220> FEATURE:
<221> NAME/KEY: misc_feature
<222> LOCATION: (1917)..(4577)
<223> OTHER INFORMATION: DNA encoding FCE mRNA Capping enzyme (878 aa) +
      8xHis-tag
<220> FEATURE:
<221> NAME/KEY: misc_feature
<222> LOCATION: (2559)..(2561)
<223> OTHER INFORMATION: asparagine to glutamine variant codon
<220> FEATURE:
<221> NAME/KEY: misc_feature
<222> LOCATION: (2925)..(2927)
<223> OTHER INFORMATION: asparagine to glutamine variant codon
<220> FEATURE:
<221> NAME/KEY: misc_feature
<222> LOCATION: (3630)..(3632)
<223> OTHER INFORMATION: asparagine to glutamine variant codon
<220> FEATURE:
<221> NAME/KEY: misc_feature
<222> LOCATION: (3858)..(3860)
<223> OTHER INFORMATION: asparagine to glutamine variant codon
<220> FEATURE:
<221> NAME/KEY: misc_feature
<222> LOCATION: (4413)..(4415)
<223> OTHER INFORMATION: asparagine to glutamine variant codon

<400> SEQUENCE: 26
gcttcagcag agcgcagata ccaaatactg ttcttctagt gtagccgtag ttaggccacc    60
acttcaagaa ctctgtagca ccgcctacat acctcgctct gctaatcctg ttaccagtgg   120
ctgctgccag tggcgataag tcgtgtctta ccgggttgga ctcaagacga tagttaccgg   180
ataaggcgca gcggtcgggc tgaacggggg gttcgtgcac acagcccagc ttggagcgaa   240
cgacctacac cgaactgaga tacctacagc gtgagctatg agaaagcgcc acgcttcccg   300
aagggagaaa ggcggacagg tatccggtaa gcggcagggt cggaacagga gagcgcacga   360
gggagcttcc aggggaaac gcctggtatc tttatagtcc tgtcgggttt cgccacctct   420
gacttgagcg tcgattttg tgatgctcgt caggggggcg gagcctatgg aaaaacgcca   480
gcaacgcggc cttttacgg ttcctggcct tttgctggcc ttttgctcac atgttctttc   540
ctgcggtacc cagatccaat tcccgctttg actgcctgaa atctccatcg cctacaatga   600
tgacatttgg atttggttga ctcatgttgg tattgtgaaa tagacgcaga tcgggaacac   660
tgaaaaatac acagttatta ttcatttaaa taacatccaa agacgaaagg ttgaatgaaa   720 ccttttttgcc atccgacatc cacaggtcca ttctcacaca taagtgccaa acgcaacagg   780 agggcgataca ctagcagcag accgttgcaa acgcaggacc tccactcctc ttctcctcaa   840
cacccacttt tgccatcgaa aaccagccc agttattggg cttgattgga gctcgctcat   900
tccaattcct tctattaggc tactaacacc atgactttat tagcctgtct atcctggccc   960
ccctggcgag gttcatgttt gtttatttcc gaatgcaaca agctccgcat tacacccgaa  1020
catcactcca gatgagggct ttctgagtgt ggggtcaaat agtttcatgt tccccaaatg  1080
gcccaaaact gacagtttaa acgctgtctt ggaacctaat atgacaaaag cgtgatctca  1140
tccaagatga actaaggatc ctttttttgta gaaatgtctt ggtgtcctcg tccaatcagg  1200
tagccatctc tgaaatatct ggctccgttg caactccgaa cgacctgctg caacgtaaa   1260 attctccggg gtaaaactta atgtggagt aatggaacca gaaacgtctc ttccctttctc  1320 tctccttcca ccgcccgtta ccgtccctag gaaatttttac tctgctggag agcttcttct  1380
acggccccct tgcagcaatg ctcttcccag cattacgttg cgggtaaaac ggaggtcgtg  1440
tacccgacct agcagcccag ggatggaaaa gtcccggccg tcgctggcaa taatagcggg  1500
cggacgcatg tcatgagatt attggaaacc accagaatcg aatataaaag gcgaacacct  1560
```

-continued

```
ttcccaattt tggtttctcc tgacccaaag actttaaatt taatttattt gtccctattt    1620
caatcaattg aacaactatt tccgaaacga tgagattccc atctattttc accgctgtct    1680
tgttcgctgc ctcctctgca ttggctgccc ctgttaacac taccactgaa gacgagactg    1740
ctcaaattcc agctgaagca gttatcggtt actctgacct tgagggtgat ttcgacgtcg    1800
ctgttttgcc tttctctaac tccactaaca acggtttgtt gttcattaac accactatcg    1860
cttccattgc tgctaaggaa gagggtgtct ctctcgagaa aagagaggcc gaagctgcga    1920
agcgtctgca gcgttgccaa gatgtgaacc aggtttgcga aatctacaac agcaagggtg    1980
gcattggcga gctggaactg cgtttcgaca aactgccgca gaacctgttc gcgggcgtgt    2040 tgataagct gaaaccggac ggcgagatcc aaaccaccat gcgtgtgagc aaccgtgacg    2100
gtgttgcgcg tgaaattacc ttcggtggcg gtgtgaaaac caacgagatc ttcgttaaga    2160
aacaaaacat ttgcgtgttc gacgtggttg atatctttag ctacaaggtg gcggttagca    2220
ccgaggaaac cgtggttgaa aaccgaccca tggagaccac cgcgggcgtt cgtttcaaaa    2280
tccgtctgag cgtggaagac gtggttaagg attggcgtat tgacctgacc gcggttaaga    2340
ccgcggagct gggtaaaatc gcgcagcaca ccgcgagcat tgtgcaacgt accttccggg    2400
ataacctgct gaagctgacc ggtgcggaag tggcgaaact ggcggcggac agctacgagc    2460
tggaactgga gtataccggc aagagcccgg cgaccaacga aaaggtgaac gttgcggcga    2520
aatacgcggt ggagctgctg agcagcgttc gtaacgcgca aagcaccgcg gcggcgagct    2580
ttggtgaaag cgtgagcgac ctgtgccgtg ttgcgaaaat cattcacacc cacgagtacg    2640
cgaacgtggt ttgccgtacc ccgagcttta aaatgctgct gccgcaggtg gttagcctga    2700
ccaagagcag ctactatggc ggtctgtatc cgccggaaaa cctgtggctg gcgggcaaga    2760
ccgatggtgt tcgtgcgctg gttgtgtgcg aagacgcgt ggcgaaagtt atcaccgcgg    2820
agagcgtgga tattacccac ggtgtttgca gcgcgaccac catcctggat tgcgagctga    2880
acgtggacgc gaagattctg tacgtgttcg acgttatcat tagccaaaac acccaggttt    2940
atacccaacc gtttagcacc cgtatcacca ccgacattag cgatatcaag atcgatggtt    3000
acaagatcga aatgaagccg ttcgtgaagg tggttaaagc ggacgaggcg accttttaaga    3060 gcgcgtataa agcgccgcac aacgaaggcc tgatcatgat tgaggatggt gcggcgtacg    3120
cggcgaccaa gacctataag tggaaaccgc tgagccacaa caccatcgat ttcctgatta    3180
aggcgtgccc gaaacagctg atcaacgttg acccgtacaa gccgcgtgcg ggttataaac    3240
tgtggctgct gttcaccacc attagcctgg atcagcaacg tgaactgggc atcgagttta    3300
ttccggcgtg gaaaatcctg ttcaccgaca ttaacatgtt tggtagccgt gttccgatcc    3360
agttccaacc ggcgattaac ccgctggcgt acgtgtgcta tctgccggaa gacgtgaacg    3420
ttaacgacgg cgatatcgtg gagatgcgtg cggttgacgg ttacgatacc attccgaaat    3480
gggaactggt gcgtagccgt aacgatcgta gaacgagcc gggcttttac ggtaacaact    3540
ataaaatcgc gagcgacatt tacctgaact atatcgatgt gttccacttt gaagacctgt    3600
acaagtataa cccgggctac ttcgagaagc aaaaaagcga tatctatgtt gcgccgaaca    3660
agtaccgtcg ttatctgatt aaaagccgt ttggtcgtta cctgcgtgat gcgaaatggg    3720
ttattgatgc ggcggcgggt cgtggtgcgg acctgcacct gtataaagcg gaatgcgtgg    3780
agcacctgct ggcgatcgac attgatccga ccgcgatcag cgaactggtt cgtcgtcgta    3840
acgagattac cggctaccaa aagagccacc gtggcggtcg taacatgcac agccaccgtg    3900
gtcagagcca ctgcgcgaaa agcaccagcc tgcacgcgct ggttgcggat ctgcgtgaaa    3960
```

```
acccggacgt gctgatcccg aagatcattc aaagccgtcc gcacgagcgt tgctacgatg    4020
cgatcgtgat taacttcgcg attcactatc tgtgcgacac cgatgaacac atccgtgact    4080
ttctgattac cgttagccgt ctgctggcgc cgaacggtgt gttcatcttt accaccatgg    4140
atggtgaaag cattgttaag ctgctggcgg accacaaagt tcgtccgggt gaagcgtgga    4200
ccatccacac cggtgatgtt aacagcccgg acagcaccgt gccgaaatac agcatccgtc    4260
gtctgtatga cagcgataag ctgaccaaaa ccggccagca aattgaggtg ctgctgccga    4320
tgagcggtga atgaaggcg gagccgctgt gcaacatcaa aaacatcatt agcatggcgc    4380
gtaagatggg cctggatctg gttgaaagcg cgcaattcag cgtgctgtac gaggcgtatg    4440
cgcgtgacta cccggatatc tatgcgcgta tgaccccgga cgataagctg tacaacgacc    4500
tgcacaccta tgcggttttt aagcgtaaga aggtgcgag cgcgaccagc catcatcacc    4560
accaccacca ccactaaagg ttgaaggggc ggccgctcaa gaggatgtca gaatgccatt    4620
tgcctgagag atgcaggctt cattttttgat acttttttat ttgtaaccta tatagtatag    4680
gatttttttt gtcattttgt ttcttctcgt acgagcttgc tcctgatcag cctatctcgc    4740
agcagatgaa tatcttgtgg tagggtttg ggaaaatcat tcgagtttga tgttttttctt    4800
ggtatttccc actcctcttc agagtacaga agattaagtg aaaccttcgt ttgtgcggat    4860
ccttcagtaa tgtcttgttt cttttgttgc agtggtgagc cattttgact tcgtgaaagt    4920
ttctttagaa tagttgtttc cagaggccaa acattccacc cgtagtaaag tgcaagcgta    4980
ggaagaccaa gactggcata aatcaggtat aagtgtcgag cactggcagg tgatcttctg    5040
aaagtttcta ctagcagata agatccagta gtcatgcata tggcaacaat gtaccgtgtg    5100
gatctaagaa cgcgtcctac taaccttcgc attcgttggt ccagtttgtt gttatcgatc    5160
aacgtgacaa ggttgtcgat tccgcgtaag catgcatacc caaggacgcc tgttgcaatt    5220
ccaagtgagc cagttccaac aatctttgta atattagagc acttcattgt gttgcgcttg    5280
aaagtaaaat gcgaacaaat taagagataa tctcgaaacc gcgacttcaa acgccaatat    5340
gatgtgcggc acacaataag cgttcatatc cgctgggtga cttttctcgct ttaaaaaatt    5400
atccgaaaaa attttctaga gtgttgttac tttatacttc cggctcgtat aatacgacaa    5460
ggtgtaagga ggactaaacc atggctaaac tcacctctgc tgttccagtc ctgactgctc    5520
gtgatgttgc tggtgctgtt gagttctgga ctgatagact cggtttctcc cgtgacttcg    5580
tagaggacga ctttgccggt gttgtacgtg acgacgttac cctgttcatc tccgcagttc    5640
aggaccaggt tgtgccagac aacactctgg catgggtatg ggttcgtggt ctggacgaac    5700
tgtacgctga gtggtctgag gtcgtgtcta ccaacttccg tgatgcatct ggtccagcta    5760
tgaccgagat cggtgaacag ccctggggtc gtgagtttgc actgcgtgat ccagctggta    5820
actgcgtgca tttcgtcgca gaagaacagg actaacaatt gacaccttac gattatttag    5880
agagtattta ttagttttat tgtatgtata cggatgtttt attatctatt tatgcccttag    5940
tattctgtaa ctatccaaaa gtcctatctt atcaagccag caatctatgt ccgcgaacgt    6000
caactaaaaa taagcttttt atgctgttct ctcttttttt cccttcggta taattatacc    6060
ttgcatccac agattctcct gccaaatttt gcataatcct ttacaacatg ctatatggg    6120
agcacttagc gccctccaaa acccatattg cctacgcatg tataggtgtt ttttccacaa    6180
tattttctct gtgctctctt tttattaaag agaagctcta tatcggagaa gcttctgtgg    6240
ccgttatatt cggccttatc gtgggaccac attgcctgaa ttggtttgcc ccggaagatt    6300
ggggaaactt ggatctgatt accttagctg caggtaccac tgagcgtcag accccgtaga    6360
```

```
aaagatcaaa ggatcttctt gagatccttt ttttctgcgc gtaatctgct gcttgcaaac   6420
aaaaaaacca ccgctaccag cggtggtttg tttgccggat caagagctac caactctttt   6480
tccgaaggta actg                                                     6494
```

<210> SEQ ID NO 27
<211> LENGTH: 886
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<223> OTHER INFORMATION: Fully processed mature FCE variant protein

<400> SEQUENCE: 27

```
Ala Lys Arg Leu Gln Arg Cys Gln Asp Val Asn Gln Val Cys Glu Ile
1               5                   10                  15

Tyr Asn Ser Lys Gly Gly Ile Gly Glu Leu Glu Leu Arg Phe Asp Lys
            20                  25                  30

Leu Pro Gln Asn Leu Phe Ala Gly Val Phe Asp Lys Leu Lys Pro Asp
        35                  40                  45

Gly Glu Ile Gln Thr Thr Met Arg Val Ser Asn Arg Asp Gly Val Ala
    50                  55                  60

Arg Glu Ile Thr Phe Gly Gly Val Lys Thr Asn Glu Ile Phe Val
65                  70                  75                  80

Lys Lys Gln Asn Ile Cys Val Phe Asp Val Asp Ile Phe Ser Tyr
            85                  90                  95

Lys Val Ala Val Ser Thr Glu Glu Val Val Glu Lys Pro Thr Met
            100                 105                 110

Glu Thr Thr Ala Gly Val Arg Phe Lys Ile Arg Leu Ser Val Glu Asp
        115                 120                 125

Val Val Lys Asp Trp Arg Ile Asp Leu Thr Ala Val Lys Thr Ala Glu
    130                 135                 140

Leu Gly Lys Ile Ala Gln His Thr Ala Ser Ile Val Gln Arg Thr Phe
145                 150                 155                 160

Pro Asp Asn Leu Leu Lys Leu Thr Gly Ala Glu Val Ala Lys Leu Ala
                165                 170                 175

Ala Asp Ser Tyr Glu Leu Glu Leu Glu Tyr Thr Gly Lys Ser Pro Ala
            180                 185                 190

Thr Asn Glu Lys Val Asn Val Ala Ala Lys Tyr Ala Val Glu Leu Leu
        195                 200                 205

Ser Ser Val Arg Asn Ala Gln Ser Thr Ala Ala Ala Ser Phe Gly Glu
    210                 215                 220

Ser Val Ser Asp Leu Cys Arg Val Ala Lys Ile Ile His Thr His Glu
225                 230                 235                 240

Tyr Ala Asn Val Val Cys Arg Thr Pro Ser Phe Lys Met Leu Leu Pro
                245                 250                 255

Gln Val Val Ser Leu Thr Lys Ser Ser Tyr Tyr Gly Gly Leu Tyr Pro
            260                 265                 270

Pro Glu Asn Leu Trp Leu Ala Gly Lys Thr Asp Gly Val Arg Ala Leu
        275                 280                 285

Val Val Cys Glu Asp Gly Val Ala Lys Val Ile Thr Ala Glu Ser Val
    290                 295                 300

Asp Ile Thr His Gly Val Cys Ser Ala Thr Thr Ile Leu Asp Cys Glu
305                 310                 315                 320
```

```
Leu Asn Val Asp Ala Lys Ile Leu Tyr Val Phe Asp Val Ile Ile Ser
                325                 330                 335

Gln Asn Thr Gln Val Tyr Thr Gln Pro Phe Ser Thr Arg Ile Thr Thr
            340                 345                 350

Asp Ile Ser Asp Ile Lys Ile Asp Gly Tyr Lys Ile Glu Met Lys Pro
        355                 360                 365

Phe Val Lys Val Val Lys Ala Asp Glu Ala Thr Phe Lys Ser Ala Tyr
370                 375                 380

Lys Ala Pro His Asn Glu Gly Leu Ile Met Ile Glu Asp Gly Ala Ala
385                 390                 395                 400

Tyr Ala Ala Thr Lys Thr Tyr Lys Trp Lys Pro Leu Ser His Asn Thr
                405                 410                 415

Ile Asp Phe Leu Ile Lys Ala Cys Pro Lys Gln Leu Ile Asn Val Asp
                420                 425                 430

Pro Tyr Lys Pro Arg Ala Gly Tyr Lys Leu Trp Leu Leu Phe Thr Thr
            435                 440                 445

Ile Ser Leu Asp Gln Gln Arg Glu Leu Gly Ile Glu Phe Ile Pro Ala
        450                 455                 460

Trp Lys Ile Leu Phe Thr Asp Ile Asn Met Phe Gly Ser Arg Val Pro
465                 470                 475                 480

Ile Gln Phe Gln Pro Ala Ile Asn Pro Leu Ala Tyr Val Cys Tyr Leu
                485                 490                 495

Pro Glu Asp Val Asn Val Asn Asp Gly Asp Ile Val Glu Met Arg Ala
                500                 505                 510

Val Asp Gly Tyr Asp Thr Ile Pro Lys Trp Glu Leu Val Arg Ser Arg
            515                 520                 525

Asn Asp Arg Lys Asn Glu Pro Gly Phe Tyr Gly Asn Asn Tyr Lys Ile
        530                 535                 540

Ala Ser Asp Ile Tyr Leu Asn Tyr Ile Asp Val Phe His Phe Glu Asp
545                 550                 555                 560

Leu Tyr Lys Tyr Asn Pro Gly Tyr Phe Glu Lys Gln Lys Ser Asp Ile
                565                 570                 575

Tyr Val Ala Pro Asn Lys Tyr Arg Arg Tyr Leu Ile Lys Ser Leu Phe
                580                 585                 590

Gly Arg Tyr Leu Arg Asp Ala Lys Trp Val Ile Asp Ala Ala Ala Gly
            595                 600                 605

Arg Gly Ala Asp Leu His Leu Tyr Lys Ala Glu Cys Val Glu His Leu
        610                 615                 620

Leu Ala Ile Asp Ile Asp Pro Thr Ala Ile Ser Glu Leu Val Arg Arg
625                 630                 635                 640

Arg Asn Glu Ile Thr Gly Tyr Gln Lys Ser His Arg Gly Gly Arg Asn
                645                 650                 655

Met His Ser His Arg Gly Gln Ser His Cys Ala Lys Ser Thr Ser Leu
                660                 665                 670

His Ala Leu Val Ala Asp Leu Arg Glu Asn Pro Asp Val Leu Ile Pro
            675                 680                 685

Lys Ile Ile Gln Ser Arg Pro His Glu Arg Cys Tyr Asp Ala Ile Val
        690                 695                 700

Ile Asn Phe Ala Ile His Tyr Leu Cys Asp Thr Asp Glu His Ile Arg
705                 710                 715                 720

Asp Phe Leu Ile Thr Val Ser Arg Leu Leu Ala Pro Asn Gly Val Phe
                725                 730                 735
```

```
Ile Phe Thr Thr Met Asp Gly Glu Ser Ile Val Lys Leu Leu Ala Asp
            740                 745                 750

His Lys Val Arg Pro Gly Glu Ala Trp Thr Ile His Thr Gly Asp Val
        755                 760                 765

Asn Ser Pro Asp Ser Thr Val Pro Lys Tyr Ser Ile Arg Arg Leu Tyr
    770                 775                 780

Asp Ser Asp Lys Leu Thr Lys Thr Gly Gln Gln Ile Glu Val Leu Leu
785                 790                 795                 800

Pro Met Ser Gly Glu Met Lys Ala Glu Pro Leu Cys Asn Ile Lys Asn
                805                 810                 815

Ile Ile Ser Met Ala Arg Lys Met Gly Leu Asp Leu Val Glu Ser Ala
            820                 825                 830

Gln Phe Ser Val Leu Tyr Glu Ala Tyr Ala Arg Asp Tyr Pro Asp Ile
        835                 840                 845

Tyr Ala Arg Met Thr Pro Asp Asp Lys Leu Tyr Asn Asp Leu His Thr
    850                 855                 860

Tyr Ala Val Phe Lys Arg Lys Gly Ala Ser Ala Thr Ser His His
865                 870                 875                 880

His His His His His His
            885

<210> SEQ ID NO 28
<211> LENGTH: 878
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (215)..(215)
<223> OTHER INFORMATION: Xaa can be any amino acid and optionally any
      amino acid other than asparagine
<220> FEATURE:
<221> NAME/KEY: MISC_FEATURE
<222> LOCATION: (337)..(337)
<223> OTHER INFORMATION: Xaa can be any amino acid and optionally any
      amino acid other than asparagine
<220> FEATURE:
<221> NAME/KEY: MISC_FEATURE
<222> LOCATION: (572)..(572)
<223> OTHER INFORMATION: Xaa can be any amino acid and optionally any
      amino acid other than asparagine
<220> FEATURE:
<221> NAME/KEY: MISC_FEATURE
<222> LOCATION: (648)..(648)
<223> OTHER INFORMATION: Xaa can be any amino acid and optionally any
      amino acid other than asparagine
<220> FEATURE:
<221> NAME/KEY: MISC_FEATURE
<222> LOCATION: (833)..(833)
<223> OTHER INFORMATION: Xaa can be any amino acid and optionally any
      amino acid other than asparagine

<400> SEQUENCE: 28

Ala Lys Arg Leu Gln Arg Cys Gln Asp Val Asn Gln Val Cys Glu Ile
1               5                   10                  15

Tyr Asn Ser Lys Gly Gly Ile Gly Glu Leu Glu Leu Arg Phe Asp Lys
            20                  25                  30

Leu Pro Gln Asn Leu Phe Ala Gly Val Phe Asp Lys Leu Lys Pro Asp
        35                  40                  45

Gly Glu Ile Gln Thr Thr Met Arg Val Ser Asn Arg Asp Gly Val Ala
    50                  55                  60

Arg Glu Ile Thr Phe Gly Gly Gly Val Lys Thr Asn Glu Ile Phe Val
65                  70                  75                  80
```

```
Lys Lys Gln Asn Ile Cys Val Phe Asp Val Asp Ile Phe Ser Tyr
                85                  90                  95
Lys Val Ala Val Ser Thr Glu Glu Thr Val Val Glu Lys Pro Thr Met
            100                 105                 110
Glu Thr Thr Ala Gly Val Arg Phe Lys Ile Arg Leu Ser Val Glu Asp
            115                 120                 125
Val Val Lys Asp Trp Arg Ile Asp Leu Thr Ala Val Lys Thr Ala Glu
        130                 135                 140
Leu Gly Lys Ile Ala Gln His Thr Ala Ser Ile Val Gln Arg Thr Phe
145                 150                 155                 160
Pro Asp Asn Leu Leu Lys Leu Thr Gly Ala Glu Val Ala Lys Leu Ala
                165                 170                 175
Ala Asp Ser Tyr Glu Leu Glu Leu Glu Tyr Thr Gly Lys Ser Pro Ala
            180                 185                 190
Thr Asn Glu Lys Val Asn Val Ala Ala Lys Tyr Ala Val Glu Leu Leu
        195                 200                 205
Ser Ser Val Arg Asn Ala Xaa Ser Thr Ala Ala Ala Ser Phe Gly Glu
210                 215                 220
Ser Val Ser Asp Leu Cys Arg Val Ala Lys Ile Ile His Thr His Glu
225                 230                 235                 240
Tyr Ala Asn Val Val Cys Arg Thr Pro Ser Phe Lys Met Leu Leu Pro
                245                 250                 255
Gln Val Val Ser Leu Thr Lys Ser Ser Tyr Tyr Gly Gly Leu Tyr Pro
            260                 265                 270
Pro Glu Asn Leu Trp Leu Ala Gly Lys Thr Asp Gly Val Arg Ala Leu
        275                 280                 285
Val Val Cys Glu Asp Gly Val Ala Lys Val Ile Thr Ala Glu Ser Val
    290                 295                 300
Asp Ile Thr His Gly Val Cys Ser Ala Thr Thr Ile Leu Asp Cys Glu
305                 310                 315                 320
Leu Asn Val Asp Ala Lys Ile Leu Tyr Val Phe Asp Val Ile Ile Ser
                325                 330                 335
Xaa Asn Thr Gln Val Tyr Thr Gln Pro Phe Ser Thr Arg Ile Thr Thr
            340                 345                 350
Asp Ile Ser Asp Ile Lys Ile Asp Gly Tyr Lys Ile Glu Met Lys Pro
        355                 360                 365
Phe Val Lys Val Val Lys Ala Asp Glu Ala Thr Phe Lys Ser Ala Tyr
370                 375                 380
Lys Ala Pro His Asn Glu Gly Leu Ile Met Ile Glu Asp Gly Ala Ala
385                 390                 395                 400
Tyr Ala Ala Thr Lys Thr Tyr Lys Trp Lys Pro Leu Ser His Asn Thr
                405                 410                 415
Ile Asp Phe Leu Ile Lys Ala Cys Pro Lys Gln Leu Ile Asn Val Asp
            420                 425                 430
Pro Tyr Lys Pro Arg Ala Gly Tyr Lys Leu Trp Leu Leu Phe Thr Thr
        435                 440                 445
Ile Ser Leu Asp Gln Gln Arg Glu Leu Gly Ile Glu Phe Ile Pro Ala
450                 455                 460
Trp Lys Ile Leu Phe Thr Asp Ile Asn Met Phe Gly Ser Arg Val Pro
465                 470                 475                 480
```

-continued

```
Ile Gln Phe Gln Pro Ala Ile Asn Pro Leu Ala Tyr Val Cys Tyr Leu
                485                 490                 495

Pro Glu Asp Val Asn Val Asn Asp Gly Asp Ile Val Glu Met Arg Ala
            500                 505                 510

Val Asp Gly Tyr Asp Thr Ile Pro Lys Trp Glu Leu Val Arg Ser Arg
        515                 520                 525

Asn Asp Arg Lys Asn Glu Pro Gly Phe Tyr Gly Asn Asn Tyr Lys Ile
    530                 535                 540

Ala Ser Asp Ile Tyr Leu Asn Tyr Ile Asp Val Phe His Phe Glu Asp
545                 550                 555                 560

Leu Tyr Lys Tyr Asn Pro Gly Tyr Phe Glu Lys Xaa Lys Ser Asp Ile
                565                 570                 575

Tyr Val Ala Pro Asn Lys Tyr Arg Arg Tyr Leu Ile Lys Ser Leu Phe
            580                 585                 590

Gly Arg Tyr Leu Arg Asp Ala Lys Trp Val Ile Asp Ala Ala Ala Gly
        595                 600                 605

Arg Gly Ala Asp Leu His Leu Tyr Lys Ala Glu Cys Val Glu His Leu
    610                 615                 620

Leu Ala Ile Asp Ile Asp Pro Thr Ala Ile Ser Glu Leu Val Arg Arg
625                 630                 635                 640

Arg Asn Glu Ile Thr Gly Tyr Xaa Lys Ser His Arg Gly Gly Arg Asn
                645                 650                 655

Met His Ser His Arg Gly Gln Ser His Cys Ala Lys Ser Thr Ser Leu
            660                 665                 670

His Ala Leu Val Ala Asp Leu Arg Glu Asn Pro Asp Val Leu Ile Pro
        675                 680                 685

Lys Ile Ile Gln Ser Arg Pro His Glu Arg Cys Tyr Asp Ala Ile Val
    690                 695                 700

Ile Asn Phe Ala Ile His Tyr Leu Cys Asp Thr Asp Glu His Ile Arg
705                 710                 715                 720

Asp Phe Leu Ile Thr Val Ser Arg Leu Leu Ala Pro Asn Gly Val Phe
                725                 730                 735

Ile Phe Thr Thr Met Asp Gly Glu Ser Ile Val Lys Leu Leu Ala Asp
            740                 745                 750

His Lys Val Arg Pro Gly Glu Ala Trp Thr Ile His Thr Gly Asp Val
        755                 760                 765

Asn Ser Pro Asp Ser Thr Val Pro Lys Tyr Ser Ile Arg Arg Leu Tyr
    770                 775                 780

Asp Ser Asp Lys Leu Thr Lys Thr Gly Gln Gln Ile Glu Val Leu Leu
785                 790                 795                 800

Pro Met Ser Gly Glu Met Lys Ala Glu Pro Leu Cys Asn Ile Lys Asn
                805                 810                 815

Ile Ile Ser Met Ala Arg Lys Met Gly Leu Asp Leu Val Glu Ser Ala
            820                 825                 830

Xaa Phe Ser Val Leu Tyr Glu Ala Tyr Ala Arg Asp Tyr Pro Asp Ile
        835                 840                 845

Tyr Ala Arg Met Thr Pro Asp Asp Lys Leu Tyr Asn Asp Leu His Thr
    850                 855                 860

Tyr Ala Val Phe Lys Arg Lys Lys Gly Ala Ser Ala Thr Ser
865                 870                 875
```